United States Patent [19]

Duggan

[11] Patent Number: 4,767,779

[45] Date of Patent: Aug. 30, 1988

[54] PYRAZOLINE-1-CARBOXAMIDES, COMPOSITION CONTAINING THEM, AND INSECTICIDAL METHOD OF USING THEM

[75] Inventor: Angelina J. Duggan, Lawrenceville, N.J.

[73] Assignee: FMC Corporation, Philadelphia, Pa.

[21] Appl. No.: 849,658

[22] Filed: Apr. 9, 1986

Related U.S. Application Data

[63] Continuation-in-part of Ser. No. 779,721, Sep. 24, 1985, abandoned, which is a continuation-in-part of Ser. No. 709,626, Mar. 8, 1985, abandoned, which is a continuation-in-part of Ser. No. 664,674, Oct. 25, 1984, abandoned.

[51] Int. Cl.$^4$ ................ A01N 43/56; C07D 231/06
[52] U.S. Cl. .................................... 514/403; 548/379
[58] Field of Search ..................... 548/379; 514/403

[56] References Cited

U.S. PATENT DOCUMENTS

| | | | |
|---|---|---|---|
| 4,174,393 | 11/1979 | Van Daalen et al. | 548/379 |
| 4,407,813 | 10/1983 | Ozawa et al. | 548/379 |

FOREIGN PATENT DOCUMENTS

| | | | |
|---|---|---|---|
| 0011179 | 5/1980 | European Pat. Off. | 546/197 |
| 21506 | 1/1981 | European Pat. Off. | 548/379 |
| 58424 | 8/1982 | European Pat. Off. | 548/379 |
| 113213 | 7/1984 | European Pat. Off. | 548/379 |
| 0153127 | 5/1985 | European Pat. Off. | 379/ |
| 722485 | 3/1980 | U.S.S.R. | 548/379 |

*Primary Examiner*—Mary C. Lee
*Assistant Examiner*—Kurt G. Briscoe
*Attorney, Agent, or Firm*—H. Robinson Ertelt; William Schmonsees

[57] ABSTRACT

Pyrazolines of the following formula are insecticides:

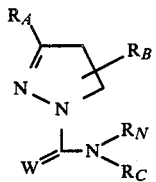

wherein $R_A$, $R_B$ and $R_C$ are aromatic groups; $R_N$ is hydrogen or lower alkyl; and W is oxygen or sulfur.

33 Claims, No Drawings

PYRAZOLINE-1-CARBOXAMIDES, COMPOSITION CONTAINING THEM, AND INSECTICIDAL METHOD OF USING THEM

This application is a continuation in part of application Ser. No. 779,721, filed Sept. 24, 1985, which is a continuation in part of application Ser. No. 709,626, filed Mar. 8, 1985, which is a continuation in part of application Ser. No. 664,674, filed Oct. 25, 1984 now abandoned.

This invention pertains to the field of bioaffecting chemical compositions; more specifically, it pertains to novel pyrazoline insecticides, processes and intermediates thereto, insecticidal compositions containing the pyrazolines, and to the use of the pyrazolines for controlling insects.

Pyrazolines are five-membered heterocyclic ring compounds with the following formula and ring atom numbering scheme:

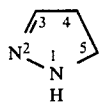

It is known in the insecticide art that certain 1-carbamoyl pyrazoline derivatives are insecticides. For example, U.S. Pat. No. 4,174,393 discloses the insecticidal activity of 1-carbamoyl pyrazolines also carrying phenyl substituents in the 3 and 4 positions of the pyrazoline ring.

It has now been found that pyrazolines of the following structural formula exhibit pronounced insecticidal activity:

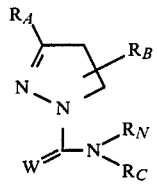

wherein
$R_A$ is of the formula

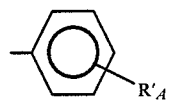

in which $R'_A$ is selected from hydrogen, halogen, lower alkyl, lower alkoxy, lower haloalkoxy, lower alkynyloxy and lower haloalkyl; or

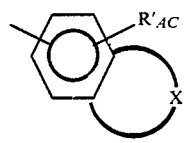

in which X is a bridge of the formula

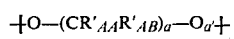

wherein a is 1-3, a' is 0 or 1, a+a' is at least 2 but no greater than 3, $R'_{AA}$ and $R'_{AB}$ are independently selected from hydrogen, halogen and lower alkyl, and $R'_{AC}$ is selected from hydrogen, halogen, lower alkyl, lower alkoxy, lower haloalkoxy, and lower haloalkyl;

$R_B$ is a 4- or 5-substituent of the formula

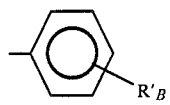

in which $R'_B$ is selected from hydrogen, halogen, lower alkyl, lower alkoxy, and lower haloalkyl; or

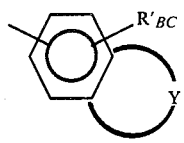

in which Y is a bridge of the formula

wherein b is 1-3, b' is 0 or 1, b+b' is at least 2 but no greater than 3, $R'_{BA}$ and $R'_{BB}$ are independently selected from hydrogen, halogen and lower alkyl, and $R'_{BC}$ is selected from hydrogen, halogen, lower alkyl, lower alkoxy, lower haloalkoxy, and lower haloalkyl;

$R_C$ is of the formula

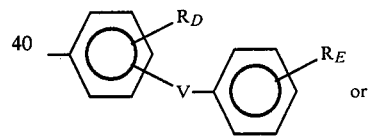

or

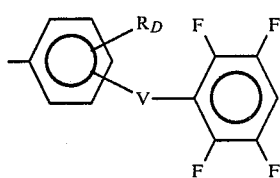

in which $R_D$ is selected from hydrogen and lower alkyl, and $R_E$ is selected from halogen, lower alkyl, lower alkoxy, lower haloalkoxy, lower haloalkyl, cyano, nitro, aryloxy, aroyl, aroyloxy, —$NR_FR_G$ wherein $R_F$ and $R_G$ are independently lower alkyl, and —$SO_nR_H$ wherein $R_H$ is lower alkyl and n is 0–2; or

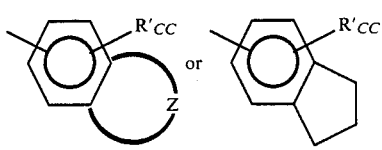

in which Z is a bridge of the formula $$\text{+O—(CR'}_{CA}\text{R'}_{CB}\text{)}_c\text{—O}_{c'}\text{+}$$

wherein c is 1–3, c' is 0 or 1, c+c' is at least 2 but no greater than 3, $R'_{CA}$ and $R'_{CB}$ are independently selected from hydrogen, halogen and lower alkyl, and $R'_{CC}$ is selected from hydrogen, halogen, lower alkyl, lower alkoxy, lower haloalkoxy, and lower haloalkyl;

$R_N$ is hydrogen or lower alkyl; and

V and W are independently oxygen or sulfur.

The terms "halo" and "halogen" when employed herein mean fluorine, chlorine or bromine. The term "lower" modifying "alkyl," "alkoxy," "alkynyloxy," and the like implies a straight or branched hydrocarbon chain of 1–6, preferably 1–4, carbon atoms; "halo" coupled with another term means one or more hydrogen atoms has been replaced by halogen.

Among the aforesaid pyrazolines, those compounds in which W is oxygen are preferred for most applications, especially when $R'_A$ is a 4-substituent, preferably halogen, for example, chlorine or fluorine, or lower haloalkoxy, for example, difluoromethoxy. Those pyrazolines in which $R_B$ is a 4-substituent are generally more active than the corresponding 5-substituted pyrazolines, and the compounds in which $R_B$ is phenyl carrying a substituent $R'_B$ are especially attractive. In this context it is preferred that $R'_B$ be a 4-substituent, especially halogen, for example, chlorine or fluorine.

With regard to $R_C$, the most attractive insecticides usually derive from those compounds with either a 2,3-dihydro-2,2-dimethylbenzofuran-5-yl, 2,3-dihydro-2,2,3,3-tetrafluorobenzofuran-5-yl, 2,3-dihydro-2,2,3,3-tetrafluorobenzofuran-6-yl, 2,2-difluoro-1,3-benzodioxol-5-yl, or a 2,2-dimethyl-1,3-benzodioxol-5-yl group, or a 4-phenoxyphenyl group. In the latter case it is preferred that $R_D$ be hydrogen and that $R_E$ be a 4-substituent, especially lower haloalkoxy.

Pyrazolines of this invention having noteworthy insecticidal activity include, for example, 3-(4-difluoromethoxyphenyl)-N-(2,3-dihydro-2,2-dimethylbenzofuran-5-yl)-4-phenylpyrazoline-1-carboxamide, 3,4-bis(4-fluorophenyl)-N-2,3-dihydro-2,2,3,3-tetrafluorobenzofuran-5-yl)pyrazoline-1-carboxamide, 3,4-bis(4-fluorophenyl) -N-(2,3-dihydro-2,2-dimethylbenzofuran-5-yl)pyrazoline-1-carboxamide, N-(2,3-dihydro-2,2,3,3-tetrafluorobenzofuran-5-yl)-3-(4-difluoromethoxyphenyl)-4-phenylpyrazoline-1-carboxamide, N-(2,2-difluoro-1,3-benzodioxol-5-yl)-3-(4-difluoromethoxyphenyl)-N-methyl-4-phenylpyrazoline-1-carboxamide, 3,4-bis(4-chlorophenyl)-N-(2,2-dimethyl-1,3-benzodioxol-5-yl)pyrazoline-1-carboxamide, N-(2,2-difluoro-1,3-benzodioxol-5-yl)-3,4-bis(4-fluorophenyl)pyrazoline-1-carboxamide, 3-(4-chlorophenyl)-N-(2,2-difluoro-1,3-benzodioxol-5-yl)-4-(4-fluorophenyl)pyrazoline-1-carboxamide, 3-(4-difluoromethoxyphenyl)-2,3-dihydro-2,2,3,3-tetrafluorobenzofuran-5-yl)-N-methyl-4-phenylpyrazoline-1-carboxamide, 3-(4-chlorophenyl)-N-[4-(4-difluoromethoxyphenoxy)phenyl]-4- phenylpyrazoline-1-carboxamide, N-[4-(4-difluoromethoxyphenoxy)phenyl]-3-(4-difluoromethoxyphenyl)-4-(4-fluorophenyl)pyrazoline-1-carboxamide, 3-(4-difluoromethoxyphenyl)-4-(4-fluorophenyl)-N-(2,3-dihydro-2,2,3,3-tetrafluorobenzofuran-5-yl)pyrazoline-1-carboxamide, 3-(4-difluoromethoxyphenyl)-4-(4-fluorophenyl)-N-(2,3-dihydro-2,2,3,3-tetrafluorobenzofuran-6-yl)pyrazoline-1-carboxamide, 4-(4-chlorophenyl)-N-(2,3-dihydro-2,2-dimethylbenzofuran-5-yl)-3-phenylpyrazoline-1-carboxamide, 3-(4-chlorophenyl)-4-(4-fluorophenyl)-N-(2,3-dihydro-2,2-dimethylbenzofuran-5-yl)pyrazoline-1-carboxamide, 3-(4-difluoromethoxyphenyl)-4-(4-fluorophenyl)-N-(2,3-dihydro-2,2-dimethylbenzofuran-5-yl)pyrazoline-1-carboxamide, and 4-(4-chlorophenyl)-3-(4-difluoromethoxyphenyl)-N-(2,3-dihydro-2,2-dimethylbenzofuran-5-yl)pyrazoline-1-carboxamide.

Also within the contemplation of the instant invention are insecticidal compositions comprising an insecticidally effective amount of at least one of the aforesaid pyrazolines in admixture with an agriculturally acceptable carrier. In addition, this invention includes the method of controlling insects which comprises applying to the locus where control is desired an insecticidally effective amount of at least one of the aforesaid pyrazolines.

Pyrazolines of this invention may be produced by coupling an appropriate aromatic isocyanate or isothiocyanate with an appropriately substituted pyrazoline, a process within the scope of this invention, namely:

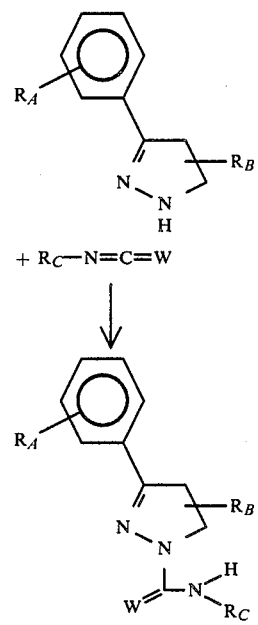

The product can be alkylated by well known methods to produce the corresponding N-alkylated pyrazolines.

The appropriately substituted pyrazoline starting materials are generally known materials. The requisite isocyanates and isothiocyanates can be prepared from the corresponding amines. A number of the amines are available in commerce. Other amines of interest can be prepared by the methods described in European patent application No. 0 011 179 and the following Examples.

EXAMPLE 1

3-(4-Chlorophenyl)-N-[4-(4-chlorophenoxy)phenyl]-4-phenylpyrazoline-1-carboxamide Under a dry nitrogen atmosphere a stirred mixture of 10.9 g (0.077 mole) 4-fluoronitrobenzene, 9.95 g (0.0077 mole) 4-chlorophenol, and 11.8 g (0.085 mole) potassium carbonate in 175 mL of dimethylsulfoxide was heated at 70° C. for two days. The reaction mixture was cooled and filtered. The filtrate was diluted with water until a volume of one liter was obtained. This mixture was extracted with three 200 mL portions of diethyl ether. The combined ether extract was washed with water followed by an aqueous saturated sodium chloride solution. The washed extract was dried over anhydrous sodium sulfate and filtered. Evaporation of the filtrate under reduced pressure yielded 13.5 g 4-(4-chlorophenoxy)nitrobenzene (mp 67°–70° C.).

Hydrogenation of 13.5 g (0.054 mole) 4-(4-chlorophenoxy)nitrobenzene with a catalytic amount (0.15 g) of platinum oxide in 250 mL of tetrahydrofuran produced a quantative yield of 4-(4-chlorophenoxy)aniline.

To a stirred solution of 0.75 g (0.0034 mole) 4-(4-chlorophenoxy)aniline in 25 mL of toluene was added dropwise a solution of 0.43 mL (0.0036 mole) trichloromethylchloroformate in 20 mL of toluene. After complete addition, the mixture was heated at 85° C. for three hours. This mixture was cooled to room temperature and the solvent evaporated under reduced pressure to leave a residue. The residue was dissolved in 25 mL of diethyl ether. This solution was added dropwise to a stirred slurry of 1.0 g (0.0034 mole) of 3-(4-chlorophenyl)-4-phenylpyrazoline in diethyl ether. Three drops of triethylamine were added and the mixture was stirred at room temperature for two days. The solvent was evaporated from the mixture to yield 0.92 g of 3-(4-chlorophenyl)-N-[4-(4-chlorophenoxy)phenyl]-4-phenylpyrazoline-1-carboxamide (mp 158°–161° C.).

Analysis: Calc. C,66.92; H,4.22, Found C,66.06; H,4.95.

nmr: 8.06 ppm (CDCl$_3$).

EXAMPLE 2

3-(4-Chlorophenyl)-N-(2,3-dihydro-2,2-dimethylbenzofuran-5-yl)-4-phenylpyrazoline-1-carboxamide During a one hour period an ice cold mixture of 43 mL concentrated nitric acid and 50 mL of concentrated sulfuric acid was added dropwise to 100.0 g (0.67 mole) 2,3-dihydro-2,2-dimethylbenzofuran while maintaining the temperature of 5° C. After complete addition the mixture was stirred at 0° C. for 2.5 hours. The reaction mixture was poured into ice water and the total extracted with diethyl ether. The extract was dried over anhydrous magnesium chloride and filtered. Evaporation of the filtrate under reduced pressure produced a black oil. Purification of this oil by column chromatography on silica gel eluting with toluenen-hexane (9:1), yielded 50.0 g of 2,3-dihydro-2,2-dimethyl-5-nitrobenzofuran as a solid.

Hydrogenation of 20.0 g (0.1 mole) 2,3-dihydro-2,2-dimethyl-5-nitrobenzofuran with a catalytic amount (0.2 g) of platinum oxide in 250 mL of methanol produced 16.6 g of 5-amino-2,3-dihydro-2,2-dimethylbenzofuran.

A solution of 0.43 mL (0.0036 mole) trichloromethylchloroformate in 20 mL of toluene was added dropwise to a stirred solution of 0.56 g (0.0034 mole) 5-amino-2,3-dihydro-2,2-dimethylbenzofuran in 20 mL of toluene. Upon complete addition the mixture was heated at reflux for three hours. The mixture was cooled to room temperature and the solvent was evaporated under reduced pressure leaving a residue. The residue was dissolved in 25 mL dry diethyl ether and the solution added dropwise to a stirred mixture of 1.0 g (0.0034 mole) 3-(4-chlorophenyl)-4-phenylpyrazoline and three drops of triethylamine in 25 mL of diethyl ether. The reaction mixture was stirred at room temperature for approximately 18 hours, at which time a solid was filtered from the mixture. The filter cake was slurried in ethanol and recovered by filtration to yield 0.47 g of 3-(4-chlorophenyl)-N- 0 (2,3-dihydro-2,2-dimethylbenzofuran-5-yl)-4-phenylpyrazoline-1-carboxamide (mp 160°–162° C.).

Analysis: Calc. C,70.00; H,5.43, Found C,69.50; H,3.36, nmr: 9.00 ppm (DMSO-d$_6$).

Other members of the series, which may be prepared by similar techniques, are represented by the following additional Examples. Melting points are given in degrees Celsius. The nmr singlet corresponding to the =NH proton, characteristic of these compounds, is also given in some cases. Unless stated otherwise, the nmr solvent is CDCl$_3$. Elemental analyses are shown in some instances.

EXAMPLE 3

3,4-Diphenyl-N-(4-phenoxyphenyl)pyrazoline-1-carboxamide, mp 184–188. 9.17 ppm (DMSO-d$_6$).

EXAMPLE 4

N-[4-(4-Chlorophenoxy)phenyl]-3,4-diphenylpyrazoline-1-carboxamide, mp 146–149. 8.83 ppm (DMSO-d$_6$).

EXAMPLE 5

3-(4-Chlorophenyl)-N-(4-phenoxyphenyl)-4-phenylpyrazoline-1-carboxamide, mp 163–166. 8.03 ppm.

EXAMPLE 6

N-(4-Phenoxyphenyl)-4-phenyl-3-(4-trifluoromethylphenyl)pyrazoline-1-carboxamide, mp 188–190. 8.10 ppm

EXAMPLE 7

3,4-bis(4-Chlorophenyl)-N-(4-phenoxyphenyl)-pyrazoline-1-carboxamide, mp 189–193. 8.20 ppm (CDCl$_3$/DMSO-d$_6$).

EXAMPLE 8

3-(4-Chlorophenyl)-N-(3-methyl-4-phenoxyphenyl)-4-phenylpyrazoline-1-carboxamide, mp 151–157. 9.13 ppm (DMSO-d$_6$).

EXAMPLE 9

3-(4-Chlorophenyl)-N-[4-(2-fluorophenoxy)phenyl]-4-phenylpyrazoline-1-carboxamide, mp 153–155. 8.16 ppm

EXAMPLE 10

3-(4-Chlorophenyl)-N-[4-(3-fluorophenoxy)phenyl]-4-phenylpyrazoline-1-carboxamide, mp 173–175. 9.33 ppm (DMSO-d$_6$).

EXAMPLE 11

N-[4-(3-Chlorophenoxy)phenyl]-3-(4-chlorophenyl)-4-phenylpyrazoline-1-carboxamide, mp 169–174. 9.30 ppm (DMSO-d$_6$).

EXAMPLE 12

3-(4-Chlorophenyl)-N-[4-(4-fluorophenoxy)phenyl]-4-phenylpyrazoline-1-carboxamide, mp 164–167. 8.13 ppm.

EXAMPLE 13

3-(4-Chlorophenyl)-N-[4-(4-trifluoromethylphenoxy)-phenyl]-4-phenylpyrazoline-1-carboxamide, mp 161–164. 8.03 ppm.

EXAMPLE 14

N-[4-(4-Chlorophenoxy)phenyl]-3-(4-difluoromethoxyphenyl)-4-phenylpyrazoline-1-carboxamide, mp 103–107. 8.00 ppm.

EXAMPLE 15

3,4-bis(4-Chlorophenyl)-N-(3-methyl-4-phenoxyphenyl)-pyrazoline-1-carboxamide, mp 188–190. 9.23 ppm (DMSO-$d_6$).

EXAMPLE 16

3,4-bis(4-Chlorophenyl)-N-[4-(2-fluorophenoxy)-phenyl]pyrazoline-1-carboxamide, mp 160–162. 8.10 ppm.

EXMAPLE 17

3,4-bis(4-Chlorophenyl)-N-[4-(3-fluorophenoxy)-phenyl]-pyrazoline-1-carboxamide, mp 144–146. 9.20 ppm (DMSO-$d_6$).

EXAMPLE 18

N-[4-(3-Chlorophenoxy)phenyl]-3,4-bis(4-chlorophenyl)pyrazoline-1-carboxamide, mp 135–140. 9.30 ppm (DMSO-$d_6$).

EXAMPLE 19

3,4-bis(4-Chlorophenyl)-N-[4-(4-fluorophenoxy)-phenyl]pyrazoline-1-carboxamide, mp 168–170. 9.23 ppm (DMSO-$d_6$).

EXAMPLE 20

N-[4-(4-Chlorophenoxy)phenyl]-3,4-bis(4-chlorophenyl)pyrazoline-1-carboxamide, mp 154–156. 9.30 ppm (DMSO-$d_6$).

EXAMPLE 21

3,4-bis(4-Chlorophenyl)-N-[4-(4-trifluoromethylphenoxy)phenyl]-pyrazoline-1-carboxamide, mp 191–194. 9.30 ppm (DMSO-$d_6$).

EXAMPLE 22

3-(4-Chlorophenyl)-4-phenyl-N-(4-phenylthiophenyl)pyrazoline-1-carboxamide, mp 157–162. 8.20 ppm.

EXAMPLE 23

3,4-bis(4-Chlorophenyl)-N-(4-phenylthiophenyl)-pyrazoline-1-carboxamide, mp 169–171. 8.20 ppm.

EXAMPLE 24

3,5-bis(4-Chlorophenyl)-N-(4-phenoxyphenyl)-pyrazoline-1-carboxamide, mp 168–170. 8.30 ppm (CDCl$_3$/DMSO-$d_6$).

EXAMPLE 25

3-(4-Chlorophenyl)-5-(4-trifluoromethylphenyl)-N-(4-phenoxyphenyl)pyrazoline-1-carboxamide, mp 164–167. 8.00 ppm.

EXAMPLE 26

3,5-bis(4-Chlorophenyl)-N-[4-(2-fluorophenoxy)-phenyl]pyrazoline-1-carboxamide, mp 174–178. 8.50 ppm.

EXAMPLE 27

3,5-bis(4-Chlorophenyl)-N-[4-(3-fluorophenoxy)-phenyl]pyrazoline-1-carboxamide, mp 164–168. 9.00 ppm (DMSOd$_6$).

EXAMPLE 28

3,5-bis(4-Chlorophenyl)-N-[4-(4-fluorophenoxy)-phenyl]pyrazoline-1-carboxamide, mp 165–167. 9.16 ppm (DMSO-$d_6$).

EXAMPLE 29

N-[4-(4-Chlorophenoxy)phenyl]-3,5-bis(4-chlorophenyl)pyrazoline-1-carboxamide, mp 142–144. 9.20 ppm (DMSO-$d_6$).

EXAMPLE 30

3,5-bis(4-Chlorophenyl)-N-[4-(4-trifluoromethylphenoxy)phenyl]-pyrazoline-1-carboxamide, mp 155–158. 8.43 ppm (CDCl$_3$/DMSO-$d_6$).

EXAMPLE 31

3-(4-Chlorophenyl)-N-[4-(4-trifluoromethylphenoxy)phenyl]-5-(4-trifluoromethylphenyl)pyrazoline-1-carboxamide, mp 144–146. 8.06 ppm.

EXAMPLE 32

N-[4-(4-Chlorophenoxy)phenyl]-5-(4-chlorophenyl)-3-(4-difluoromethoxyphenyl)pyrazoline-1-carboxamide, mp 66–70. 8.60 ppm (DMSO-$d_6$).

EXAMPLE 33

5-(1,3-Benzodioxol-5-yl)-3-(4-chlorophenyl)-N-(4-phenoxyphenyl)-pyrazoline-1-carboxamide, mp 125–128. 8.36 ppm (CDCl$_3$/DMSO-$d_6$).

EXAMPLE 34

5-(1,3-Benzodioxol-5-yl)-N-[4-(4-chlorophenoxy)-phenyl]-3-(4-chlorophenyl)pyrazoline-1-carboxamide, mp 174–175. 8.06 ppm.

EXAMPLE 35

N-(2,3-Dihydro-2,2-dimethylbenzofuran-5-yl)-3,4-diphenylpyrazoline-1-carboxamide, mp 139–143. 7.96 ppm.

EXAMPLE 36

3-(4-Difluoromethoxyphenyl)-N-(2,3-dihydro-2,2-dimethylbenzofuran-5-yl)-4-phenylpyrazoline-1-carboxamide, mp 75–82. 7.96 ppm.

EXAMPLE 37

(±)-3,4-bis(4-Chlorophenyl)-N-(2,3-dihydro-2,2-dimethylbenzofuran-5-yl)pyrazoline-1-carboxamide, mp 134–137. 7.93 ppm.

EXAMPLE 37a (±)-3,4-bis(4-Chlorophenyl)-N-(2,3-dihydro-2,2-dimethylbenzofuran-5-yl)pyrazoline-1-carboxamide, mp 134–137.

EXAMPLE 37b (−)-3,4-bis(4-Chlorophenyl)-N-(2,3-dihydro-2,2-dimethylbenzofuran-5-yl)pyrazoline-1-carboxamide, mp 134–137.

EXAMPLE 38

3,5-bis(4-Chlorophenyl)-N-(2,3-dihydro-2,2-dimethylbenzofuran-5-yl)pyrazoline-1-carboxamide, mp 175–180. 8.86 ppm (DMSO-$d_6$)

EXAMPLE 39

N-(1,4-Benzodioxan-6-yl)-3-(4-chlorophenyl)-4-phenylpyrazoline-1-carboxamide, mp 112–115. 7.96 ppm.

EXAMPLE 40

N-(1,4-Benzodioxan-6-yl)-3,4-bis(4-chlorophenyl)-pyrazoline-1-carboxamide, mp 140–145. 7.96 ppm.

EXAMPLE 41

3-(4-Chlorophenyl)-N-(4-phenoxyphenyl)-4-phenylpyrazoline-1-carbothioamide, mp 105–110. 10.30 ppm (DMSO-$d_6$).

EXAMPLE 42

3,4-bis(4-Chlorophenyl)-N-(4-phenoxyphenyl)-pyrazoline-1-carbothioamide, mp 151–153. 9.26 ppm (DMSO-$d_6$).

EXAMPLE 43

N-[4-(4-Chlorophenoxy)phenyl]-3,4-bis(4-chlorophenyl)pyrazoline-1-carbothioamide, mp 179–183. 9.10 ppm.

EXAMPLE 44

3-(4-Chlorophenyl)-N-(2,3-dihydro-2,2-dimethylbenzofuran-5-yl)-4-phenylpyrazoline-1-carbothioamide, mp 92–95. 10.12 ppm (DMSO-$d_6$).

EXAMPLE 45

3,4-bis(4-Chlorophenyl)-N-(2,3-dihydro-2,2-dimethylbenzofuran-5-yl)pyrazoline-1-carbothioamide, mp 149–154. 9.00 ppm (DMSO-$d_6$).

EXAMPLE 46

N-(1,4-Benzodioxan-6-yl)-3,5-bis(4-chlorophenyl)-pyrazoline-1-carboxamide, mp 83–85. 9.33 ppm (DMSO-$d_6$).

EXAMPLE 47

5-(4-Chlorophenyl-3-(4-trifluoromethylphenyl)-N-[4-(4-trifluoromethylphenoxy)phenyl]pyrazoline-1-carboxamide, mp 183–185. 8.77 ppm (CDCl$_3$/DMSO-$d_6$).

EXAMPLE 48

N-(2,3-Dihydro-2,2,3,3-tetrafluorobenzofuran-5-yl)-3-(4-difluoromethoxyphenyl)-4-phenylpyrazoline-1-carboxamide Into a pressure bottle was placed 15.0 g (0.086 mole) 2-chloro-4-nitrophenol, 11.9 g (0.086 mole) potassium carbonate, 1.5 g (0.02 mole) propanethiol, 33.7 g (0.13 mole) 1,2-dibromotetrafluoroethane and 115 mL of N,N-dimethylformamide. The pressure bottle was sealed and the mixture stirred at 50° C. for 48 hours. The pressure bottle was cooled to room temperature, opened, and the contents poured into a separatory funnel. Approximately 200 mL of a 2N sodium hydroxide solution was added to the separatory funnel. The resultant mixture was extracted with four 300 mL portions of diethyl ether. The extracts were combined and washed with two 100 mL portions of a 2N sodium hydroxide solution. The washed extract was dried over anhydrous magnesium sulfate and filtered. The filtrate was evaporated under reduced pressure leaving an oil. The reaction described above was repeated three additional times. The residual oils from the four experiments were combined and purified by column chromatography on silica gel, eluting with n-heptane:toluene (95:5), to yield 57.6 g of 3-chloro4-(2-bromo-1,1,2,2-tetrafluoroethoxy)nitrobenzene as an oil.

Into a pressure bottle was placed 10.0 g (0.028 mole) 3-chloro-4-(2-bromo-1,1,2,2-tetrafluoroethoxy)nitrobenzene, 9.0 g (0.14 mole) copper powder (200 mesh), 0.45 g (0.0028 mole) 2,2'-bipyridyl, and 40 mL of dimethylsulfoxide. The pressure bottle was sealed and the reaction mixture stirred at 190°–195° C. for two hours. The pressure bottle was cooled to room temperature, opened, and the contents poured into a separatory funnel. Approximately 200 mL of a 2N hydrochloric acid solution was added to the separatory funnel. The mixture was extracted with three 150 mL portions of diethyl ether. The extracts were combined and washed in succession with 200 mL of a 2N hydrochloric acid solution, 200 mL of a saturated aqueous sodium chloride solution, and 200 mL of a 2N sodium hydroxide solution. The washed extract was dried over anhydrous magnesium sulfate and filtered. The solvent was evaporated under reduced pressure leaving an oil. The reaction described above was repeated six additional times. The residual oils from the seven experiments were combined and subjected to column chromatography on silica gel, eluting with toluene, to yield a yellow oil. This oil was dissolved in 125 mL methylcyclohexane and the solution placed in a freezer for approximately 18 hours. Crystals had formed and were collected by filtration to yield 20.7 g 2,3-dihydro-2,2,3,3-tetrafluoro-5-nitrobenzofuran. The filtrate was evaporated under reduced pressure leaving an oil. Distillation of this oil under reduced pressure provided an additional 3.0 g of product (bp 75° C./0.2 mm). Hydrogenation of 2.15 g (0.011 mole) 2,3-dihydro-2,2,3,3-tetrafluoro-5-nitrobenzofuran with a catalytic amount (0.25 g) of platinum oxide in 150 mL of methanol produced 2.15 g of 5-amino-2,3-dihydro-2,2,3,3-tetrafluorobenzofuran.

A solution of 0.75 g (0.0036 mole) 5-amino-2,3-dihydro-2,2,3,3-tetrafluorobenzofuran dissolved in 109 mL of toluene was added dropwise to a stirred solution of 8.0 mL 20% phosgene in toluene. After complete addition the mixture was heated at reflux for two hours. The mixture was cooled and the solvent removed by evaporation under reduced pressure leaving a residue. This residue was dissolved in 15 mL of diethyl ether and added to a stirred solution of 1.04 g (0.0036 mole) 3-(4-difluoromethoxyphenyl)-4-phenylpyrazoline and three drops of triethylamine in 100 mL of diethyl ether. After complete addition the mixture was heated at reflux for one hour, then cooled to room temperature and stirred for approximately 18 hours. The solvent was removed from the reaction mixture by evaporation under reduced pressure leaving a solid residue. Recrystallization from ethanol provided 0.99 g of N-(2,3-dihydro-2,2,3,3-tetrafluorobenzofuran-5-yl)-3-(4-difluoromethoxyphenyl)-4-phenylpyrazoline-1-carboxamide (mp 155°–159° C.).

Analysis: Calc. C,58.58; H,3.29, Found C,57.81; H,3.75.

nmr: 8.16 ppm.

EXAMPLE 49

3,4-bis(4-Chlorophenyl)-N-(2,2-difluoro-1,3-benzodioxol-5-yl)pyrazoline-1-carboxamide A solution of 1.18 g (0.0068 mole) 5-amino-2,2-difluoro-1,3-benzodioxole, prepared by the method described in the literature and dissolved in 80 mL of tetrahydrofuran, was added dropwise to a cold (5° to 10° C.) solution of 24 mL 20% phosgene in toluene. After complete addition the mixture was stirred at 2° C. for one hour, then at reflux for 2 hours. The solvent was evaporated under reduced pressure to leave 1.4 g of a liquid residue. In a clean reaction flask 0.68 g of this residue was added slowly to a stirred solution of 0.93 g (0.0032 mole) 3,4-bis(4-chlorophenyl)pyrazoline and three drops of triethylamine in 20 mL of diethyl ether. After complete addition the mixture was stirred at room temperature for approximately 18 hours. A small amount of solid was present in the reaction mixture and was removed by filtration. The filtrate was evaporated under reduced pressure leaving a residue. Purification of this residue by column chromatography on silica gel, eluting with n-heptane: ethyl acetate (1:1), produced 1.3 g of 3,4-bis(4-chlorophenyl)-N-(2,2-difluoro-1,3-benzodioxol-5-yl)-pyrazoline-1-carboxamide, (mp 150°–155° C.).

Analysis: Calc. C,56.34; H,3.08, Found C,57.16; H,2.89.

nmr: 8.10 ppm.

The compound of Example 50 was similarly prepared.

EXAMPLE 50

N-(2,2-Difluoro-1,3-benzodioxol-5-yl)-3-(4-difluoromethoxyphenyl)-4-phenylpyrazoline-1-carboxamide, mp 135–138. 8.10 ppm.

EXAMPLE 51

3-(4-Fluorophenyl)-N-(4-phenoxyphenyl)-4-phenylpyrazoline-1-carboxamide, mp 187–191. 8.10 ppm.

EXAMPLE 52

3-(4-Difluoromethoxyphenyl)-N-(4-phenoxyphenyl)-4-phenylpyrazoline-1-carboxamide, mp 139–144. 8.10 ppm.

EXAMPLE 53

3-(4-Chlorophenyl)-N-[4-(4-chlorophenoxy)-phenyl]-4-phenylpyrazoline-1-carboxamide, mp 170–174. 8.10 ppm.

EXAMPLE 54

3-(4-Chlorophenyl)-N-[4-(4-nitrophenoxy)phenyl]-4-phenylpyrazoline-1-carboxamide, mp 187–189. 8.30 ppm.

EXAMPLE 55

3-(4-Chlorophenyl)-N-[4-(4-methoxyphenoxy)-phenyl]-4-phenylpyrazoline-1-carboxamide, mp 159–160. 8.07 ppm.

EXAMPLE 56

3-(4-Chlorophenyl)-N-[4-(4-difluoromethoxyphenoxy)-phenyl]-4-phenylpyrazoline-1-carboxamide, mp 181–184. 8.07 ppm.

EXAMPLE 57

N-[4-(4-Chlorophenoxy)phenyl]-3-(4-trifluoromethoxyphenyl)-4-phenylpyrazoline-1-carboxamide, mp 132–134. 8.16 ppm.

EXAMPLE 58

N-[4-(4-Chlorophenoxy)phenyl]-4-phenyl-3-[4-(2-propynyloxy)phenyl]pyrazoline-1-carboxamide, mp 160–164. 8.13 ppm.

EXAMPLE 59

3-(1,3-Benzodioxol-5-yl)-N-(4-phenoxyphenyl)-4-phenylpyrazoline-1-carboxamide, mp 220–223. 8.06 ppm.

EXAMPLE 60

4-(4-Chlorophenyl)-N-(4-phenoxyphenyl)-3-phenylpyrazoline-1-carboxamide, mp 153–155. 8.16 ppm.

EXAMPLE 61

3,4-bis(4-Fluorophenyl)-N-(4-phenoxyphenyl)-pyrazoline-1-carboxamide, mp 194–198. 8.16 ppm.

EXAMPLE 62

N-[4-(2-Chlorophenoxy)phenyl]-3,4-bis(4-chlorophenyl)pyrazoline-1-carboxamide, mp 182–186. 8.10 ppm.

EXAMPLE 63

3,4-bis(4-Chlorophenyl)-N-[4-(4-methoxyphenoxy)-phenyl]pyrazoline-1-carboxamide, mp 134–139. 8.20 ppm.

EXAMPLE 64

3-(4-Chlorophenyl)-4-(4-fluorophenyl)-N-(4-phenoxyphenyl)pyrazoline-1-carboxamide, mp 178–179. 8.10 ppm.

EXAMPLE 65

N-[4-(4-Chlorophenoxy)phenyl]-3-(4-chlorophenyl)-4-(4-fluorophenyl)pyrazoline-1-carboxamide, mp 143–145. 8.03 ppm.

EXAMPLE 66

3-(4-Chlorophenyl)-4-(4-methylphenyl)-N-(4-phenoxyphenyl)pyrazoline-1-carboxamide, mp 165–168. 8.10 ppm.

EXAMPLE 67

N-[4-(4-Chlorophenoxy)phenyl]-3-(4-chlorophenyl)-4-(4-methoxyphenyl)pyrazoline-1-carboxamide, mp 169–173. 8.07 ppm.

EXAMPLE 68

4-(4-Fluorophenyl)-3-(4-methoxyphenyl)-N-(4-phenoxyphenyl)pyrazoline-1-carboxamide, mp 184–187. 8.17 ppm.

EXAMPLE 69

N-[4-(4-Difluoromethoxyphenoxy)phenyl]-3-(4-difluoromethoxyphenyl)-4-(4-fluorophenyl)pyrazoline-1-carboxamide. 8.10 ppm.

EXAMPLE 70

N-[4-(4-Chlorophenoxy)phenyl]-3-(4-chlorophenyl)-4-phenylpyrazoline-1-thiocarboxamide, mp 179–183. 9.10 ppm.

EXAMPLE 71

3-(4-Difluoromethoxyphenyl)-N-(4-phenoxyphenyl)-4-phenylpyrazoline-1-thiocarboxamide, mp 132–136. 9.13 ppm.

EXAMPLE 72

4-(4-Chlorophenyl)-N-(4-phenoxyphenyl)-3-phenyl-pyrazoline-1-thiocarboxamide, mp 131–133. 9.16 ppm.

EXAMPLE 73

N-[4-(4-Chlorophenylthio)phenyl]-3,4-diphenyl-pyrazoline-1-carboxamide, mp 186–190. 8.20 ppm.

EXAMPLE 74

3-(4-Chlorophenyl)-N-[4-(4-chlorophenylthio)phenyl]-4-phenylpyrazoline-1-carboxamide, mp 178–181. 8.23 ppm.

EXAMPLE 75

3-(4-Difluoromethoxyphenyl)-4-phenyl-N-(4-phenylthiophenyl)pyrazoline-1-carboxamide, mp 135–140. 8.13 ppm.

EXAMPLE 76

3,4-bis(4-Chlorophenyl)-N-[4-(4-fluorophenylthio)phenyl]pyrazoline-1-carboxamide, mp 171–175. 8.20 ppm.

EXAMPLE 77

3,4-bis(4-Chlorophenyl)-N-[4-(4-chlorophenylthio)phenyl]pyrazoline-1-carboxamide, mp 151–156. 8.13 ppm.

EXAMPLE 78

3,4-bis(4-Chlorophenyl)-N-[4-(3-chlorophenoxy)phenyl]pyrazoline-1-carboxamide, mp 135–140. 9.20 ppm (DMSO-$d_6$).

EXAMPLE 79

3-(4-methoxyphenyl)-N-(4-phenoxyphenyl)-4-phenylpyrazoline-1-carboxamide, mp 188–192. 8.46 ppm (CDCl$_3$/DMSO-$d_6$).

EXAMPLE 80

3-[4-(2-propynyloxy)phenyl]-N-(4-phenoxyphenyl)-4-phenylpyrazoline-1-carboxamide, mp 121–126. 8.10 ppm.

EXAMPLE 81

3-(4-Chlorophenyl)-N-(2,3-dihydrobenzofuran-5-yl)-4-phenylpyrazoline-1-carboxamide, mp 155–158. 7.93 ppm.

EXAMPLE 82

3-(4-Difluoromethoxyphenyl)-N-(2,3-dihydrobenzofuran-5-yl)-4-phenylpyrazoline-1-carboxamide. 7.93 ppm.

EXAMPLE 83

3,4-bis(4-Chlorophenyl)-N-(2,3-dihydrobenzofuran-5-yl)pyrazoline-1-carboxamide, mp 214–216. 7.93 ppm.

EXAMPLE 84

3-(4-Fluorophenyl)-N-(2,3-dihydro-2,2-dimethylbenzofuran-5-yl)-4-phenylpyrazoline-1-carboxamide, mp 156–160. 7.93 ppm.

EXAMPLE 85

3-(4-Methoxyphenyl)-N-(2,3-dihydro-2,2-dimethylbenzofuran-5-yl)-4-phenylpyrazoline-1-carboxamide, mp 164–169. 8.00 ppm.

EXAMPLE 86

3-(4-Trifluoromethoxyphenyl)-N-(2,3-dihydro-2,2-dimethylbenzofuran-5-yl)-4-phenylpyrazoline-1-carboxamide mp 81–83. 7.98 ppm.

EXAMPLE 87

N-(2,3-Dihydro-2,2-dimethylbenzofuran-5-yl)-4-phenyl-3-[4-(2-propynyloxy)phenyl]pyrazoline-1-carboxamide, mp 175–179. 8.00 ppm.

EXAMPLE 88

3-(1,3-Benzodioxol-5-yl)-N-(2,3-dihydro-2,2-dimethylbenzofuran-5-yl)-4-phenylpyrazoline-1-carboxamide, mp 223–227. 8.90 ppm (DMSO-$d_6$).

EXAMPLE 89

4-(4-Chlorophenyl)-N-(2,3-dihydro-2,2-dimethylbenzofuran-5-yl)-3-phenylpyrazoline-1-carboxamide. 8.00 ppm.

EXAMPLE 90

3,4-bis(4-Fluorophenyl)-N-(2,3-dihydro-2,2-dimethylbenzofuran-5-yl)pyrazoline-1-carboxamide, mp 161–166. 7.93 ppm.

EXAMPLE 91

3-(4-Chlorophenyl)-4-(4-fluorophenyl)-N-(2,3-dihydro-2,2-dimethylbenzofuran-5-yl)pyrazoline-1-carboxamide, mp 169–171. 7.96 ppm.

EXAMPLE 92

3-(4-Chlorophenyl)-4-(4-methylphenyl)-N-(2,3-dihydro-2,2-dimethylbenzofuran-5-yl)pyrazoline-1-carboxamide, mp 137–139. 7.96 ppm.

EXAMPLE 93

3-(4-Chlorophenyl)-4-(4-methoxyphenyl)-N-(2,3-dihydro-2,2-dimethylbenzofuran-5-yl)pyrazoline-1-carboxamide, mp 182–186. 7.93 ppm.

EXAMPLE 94

4-(4-Fluorophenyl)-N-(2,3-dihydro-2,2-dimethylbenzofuran-5-yl)-3-(4-methoxyphenyl)pyrazoline-1carboxamide, mp 179–182. 7.93 ppm.

EXAMPLE 95

4-(4-Chlorophenyl)-N-(2,3-dihydro-2,2-dimethylbenzofuran-5-yl)-3-(4-methoxyphenyl)pyrazoline-1carboxamide, mp 157–160. 7.96 ppm.

EXAMPLE 96

3-(4-Difluoromethoxyphenyl)-4-(4-fluorophenyl)-N-(2,3-dihydro-2,2-dimethylbenzofuran-5-yl)pyrazoline-1-carboxamide, mp 169–172. 7.93 ppm.

EXAMPLE 97

4-(4-Chlorophenyl)-3-(4-difluoromethoxyphenyl)-N-(2,3-dihydro-2,2-dimethylbenzofuran-5-yl)pyrazoline-1-carboxamide, mp 90–95. 7.93 ppm.

EXAMPLE 98

3-(4-Difluoromethoxyphenyl)-N-(2,3-dihydro-2,2,3,3-tetrafluorobenzofuran-6-yl)-4-phenylpyrazoline-1-carboxamide, mp 152–157. 8.33 ppm.

EXAMPLE 99

3-(4-Difluoromethoxyphenyl)-4-(4-fluorophenyl)-N-(2,3-dihydro-2,2,3,3-tetrafluorobenzofuran-6-yl)pyrazoline-1carboxamide, mp 110–114. 8.33 ppm.

EXAMPLE 100

3-(4-Difluoromethoxyphenyl)-4-(4-fluorophenyl)-N-(2,3-dihydro-2,2,3,3-tetrafluorobenzofuran-5-yl)pyrazoline-1-carboxamide, mp 155–159. 8.20 ppm.

EXAMPLE 101

3-(4-Chlorophenyl)-N-(2,2-dimethyl-1,3-benzodioxol-5-yl)-4-phenylpyrazoline-1-carboxamide, mp 182–186. 7.96 ppm.

EXAMPLE 102

3-(4-Difluoromethoxyphenyl)-N-(2,2-dimethyl-1,3-benzodioxol-5-yl)-4-phenylpyrazoline-1-carboxamide, mp 148–150. 7.93 ppm.

EXAMPLE 103

3,4-bis(4-Chlorophenyl)-N-(2,2-dimethyl-1,3-benzodioxol-5-yl)-pyrazoline-1-carboxamide, mp 168–169. 7.93 ppm.

EXAMPLE 104

N-(1,4-Benzodioxan-5-yl)-3-(4-difluoromethoxyphenyl)-4-phenylpyrazoline-1-carboxamide. 7.93 ppm.

EXAMPLE 105

N-(2,2-Difluoro-1,3-benzodioxol-5-yl)-3-(4-difluoromethoxyphenyl)-N-methyl-4-phenylpyrazoline-1-carboxamide, mp 110–114.

EXAMPLE 106

4-(1,3-Benzodioxol-5-yl)-N-(4-phenoxyphenyl)-3-phenylpyrazoline-1-carboxamide, mp 195–197. 8.03 ppm.

EXAMPLE 107

3-(4-Chlorophenyl)-N-[4-[4-(1,1-dimethylethyl)-Phenoxy]phenyl]-4-phenylpyrazoline-1-carboxamide, mp 192.5–194. 8.03 ppm.

EXAMPLE 108

3-(4-Chlorophenyl)-4-(4-fluorophenyl)-N-[4-(4-methylphenoxy)phenyl]pyrazoline-1-carboxamide, mp 162–164. 8.03 ppm.

EXAMPLE 109

3-(4-Chlorophenyl)-4-(4-fluorophenyl)-N-[4-[4-(1,1-dimethylethyl)phenoxy]phenyl]pyrazoline-1-carboxamide, mp 188–198. 8.03 ppm.

EXAMPLE 110

3-(4-Chlorophenyl)-N-[4-[4-(1-methylethyl)phenoxy]-phenyl]-4-phenylpyrazoline-1-carboxamide, mp 181–182.5. 8.06 ppm.

EXAMPLE 111

3-(4-Chlorophenyl)-4-(4-fluorophenyl)-N-[4-[4-(1-methylethyl)phenoxy]phenyl]pyrazoline-1-carboxamide, mp 186–187. 8.60 ppm (CDCl$_3$/DMSO-d$_6$).

EXAMPLE 112

3-(4-Chlorophenyl)-N-[4-(4-methylphenoxy)phenyl-4-phenylpyrazoline-1-carboxamide, mp 150–151. 8.06 ppm.

EXAMPLE 113

3-(4-Chlorophenyl)-N-[4-[4-(1-methylethoxy)-phenoxy]phenyl]-4-phenylpyrazoline-1-carboxamide, mp 158–160.5. 8.06 ppm.

EXAMPLE 114

3-(4-Chlorophenyl)-4-(4-fluorophenyl)-N-[4-[4-(1-methylethoxy)phenoxy]phenyl]pyrazoline-1-carboxamide, mp 213–216. 8.66 ppm (CDCl$_3$/DMSO-d$_6$).

EXAMPLE 115

3,4-bis(4-Fluorophenyl)-N-[4-[4-(1-methylethoxy)-phenoxy]phenyl]pyrazoline-1-carboxamide, mp 134–136. 8.06 ppm.

EXAMPLE 116

3,4-bis(4-Fluorophenyl)-N-[4-[4-(4-chlorophenoxy)-phenyl]pyrazoline-1-carboxamide, mp 197–198.5. 8.70 ppm (CDCl$_3$DMSO-d$_6$).

EXAMPLE 117

3,4-bis(4-Fluorophenyl)-N-[4-[4-(1,1-dimethylethyl)-phenoxy]phenyl]pyrazoline-1-carboxamide, mp 189–192. 8.70 ppm (CDCl$_3$/DMSO-d$_6$).

EXAMPLE 118

3,4-bis(4-Fluorophenyl)-N-[4-(4-cyanophenoxy)-phenyl]pyrazoline-1-carboxamide, mp 198–200. 8.13 ppm.

EXAMPLE 119

3,4-bis(4-Fluorophenyl)-N-[4-[4-(N,N-dimethylamino)phenoxy]phenyl]pyrazoline-1-carboxamide, mp 148–150. 8.02 ppm.

EXAMPLE 120

3-(4-Chlorophenyl)-N-[4-(4-cyanophenoxy)phenyl]-4-phenylpyrazoline-1-carboxamide, mp 170–172. 8.16 ppm.

EXAMPLE 121

N-(1,4-Benzodioxan-6-yl)-4-(4-chlorophenyl)-3-(4-difluoromethoxyphenyl)pyrazoline-1-carboxamide, mp 124–128. 7.93 ppm.

EXAMPLE 122

3,4-bis(4-Chlorophenyl)-N-(2,3-dihydro-2,2-dimethylbenzofuran-5-yl)-N-methylpyrazoline-1-carboxamide, mp 150–155.

EXAMPLE 123

N-(2,2-Difluoro-1,3-benzodioxol-5-yl)-3,4-diphenylpyrazoline-1-carboxamide, mp 214–216. 8.83 ppm (CDCl$_3$/DMSO-d$_6$).

EXAMPLE 124

N-(2,2-Difluoro-1,3-benzodioxol-5-yl)-3,4-bis(4-fluorophenyl)pyrazoline-1-carboxamide, mp 178–180. 8.10 ppm.

EXAMPLE 125

3-(4-Chlorophenyl)-N-(2,2-difluoro-1,3-benzodioxol-5-yl)-4-(4-fluorophenyl)pyrazoline-1-carboxamide, mp 147–151. 8.06 ppm.

EXAMPLE 126

3-(4-Difluoromethoxyphenyl)-N-(2,3-dihydro-2,2,3,3-tetrafluorobenzofuran-5-yl)-N-methyl-4-phenyl-pyrazoline-1-carboxamide.

EXAMPLE 127

3-(4-Chlorophenyl)-4-(4-difluoromethoxyphenyl)-N-(2,3-dihydro-2,2-dimethylbenzofuran-5-yl)pyrazoline-1-carboxamide, mp 155–159. 7.96 ppm.

EXAMPLE 128

3-(4-Difluoromethoxyphenyl)-N-(2,3-dihydro-2,2-difluorobenzofuran-5-yl)-N-methyl-4-phenylpyrazoline-1-carboxamide.

EXAMPLE 129

4-(4-Chlorophenyl)-N-(2,2-difluoro-1,3-benzodioxol-5-yl)-3-(4-difluoromethoxyphenyl)pyrazoline-1-carboxamide. 8.06 ppm.

EXAMPLE 130

4-(1,3-Benzodioxol-5-yl)-3-(4-chlorophenyl)-N-[4-(4-fluoromethoxyphenoxy)phenyl]pyrazoline-1-carboxamide.

EXAMPLE 131

4-(1,3-Benzodioxol-5-yl)-N-[4-(4-chlorophenoxy)-phenyl]3-(4-chlorophenyl)pyrazoline-1-carboxamide.

EXAMPLE 132

4-(1,3-Benzodioxol-5-yl)-3-(4-chlorophenyl)-N-(2,2-difluoro-1,3-benzodioxol-5-yl)pyrazoline-1-carboxamide.

EXAMPLE 133

4-(1,3-Benzodioxol-5-yl)-3-(4-chlorophenyl)-N-(2,3-dihydro-2,2,3,3-tetrafluorobenzofuran-5-yl)pyrazoline-1-carboxamide.

EXAMPLE 134

4-(1,3-Benzodioxol-5-yl)-3-(4-chlorophenyl)-N-(2,3-dihydro-2,2-dimethylbenzofuran-5-yl)pyrazoline-1-carboxamide.

EXAMPLE 135

4-(1,3-Benzodioxol-5-yl)-N-[4-(4-difluoromethoxyphenoxy)phenyl]-3-(4-difluoromethoxyphenyl)pyrazoline-1-carboxamide.

EXAMPLE 136

4-(1,3-Benzodioxol-5-yl)-N-[4-(4-chlorophenoxy)phenyl]-3-(4-difluoromethoxyphenyl)pyrazoline-1-carboxamide.

EXAMPLE 137

4-(1,3-Benzodioxol-5-yl)-N-(2,2-difluoro-1,3-benzodioxol-5-yl)-3-(4-difluoromethoxyphenyl)pyrazoline-1-carboxamide.

EXAMPLE 138

4-(1,3-Benzodioxol-5-yl)-3-(4-difluoromethoxyphenyl)-N-(2,3-dihydro-2,2,3,3-tetrafluorobenzofuran-5-yl)pyrazoline-1-carboxamide.

EXAMPLE 139

4-(1,3-Benzodioxol-5-yl)-3-(4-difluoromethoxyphenyl)-N-(2,3-dihydro-2,2-dimethylbenzofuran-5-yl)pyrazoline-1-carboxamide.

EXAMPLE 140

4-(1,3-Benzodioxol-5-yl)-N-(2,3-dihydro-2,2-dimethylbenzofuran-5-yl)--3-phenylpyrazoline-1-carboxamide.

EXAMPLE 141

4-(1,3-Benzodioxol-5-yl)-N-(2,3-dihydro-2,2,3,3-tetrafluorobenzofuran-5-yl)-3-phenylpyrazoline-1-carboxamide.

EXAMPLE 142

4-(1,3-Benzodioxol-5-yl)-N-(2,2-difluoro-1,3-benzodioxol-5-yl)-3-phenylpyrazoline-1-carboxamide.

EXAMPLE 143

4-(1,3-Benzodioxol-5-yl)-N-[4-(4-difluoromethoxyphenoxy)phenyl]-3-phenylpyrazoline-1-carboxamide.

EXAMPLE 144

4-(1,3-Benzodioxol-5-yl)-N-[4-(4-chlorophenoxy)-Phenyl]3-phenylpyrazoline-1-carboxamide.

EXAMPLE 145

4-(2,2-Difluoro-1,3-benzodioxol-5-yl)-N-[4-(4-difluoromethoxyphenoxy)phenyl]-3-(4-fluorophenyl)-pyrazoline-1-carboxamide.

EXAMPLE 146

N-[4-(4-Chlorophenoxy)phenyl]-4-(2,2-difluoro-1,3-benzodioxol-5-yl)-3-(4-fluorophenyl)pyrazoline-1-carboxamide.

EXAMPLE 147

4,N-bis(2,2-Difluoro-1,3-benzodioxol-5-yl)-3-(4-fluorophenyl)pyrazoline-1-carboxamide.

EXAMPLE 148

4-(2,2-Difluoro-1,3-benzodioxol-5-yl)-3-(4-fluorophenyl)-N-(2,3-dihydro-2,2,3,3-tetrafluorobenzofuran-5-yl)pyrazoline-1-carboxamide.

EXAMPLE 149

4-(2,2-Difluoro-1,3-benzodioxol-5-yl)-3-(4-fluorophenyl)-N-(2,3-dihydro-2,2-dimethylbenzofuran-5-yl)-pyrazoline-1-carboxamide.

EXAMPLE 150

4-(2,2-Difluoro-1,3-benzodioxol-5-yl)-N-[4-(4-difluoromethoxyphenoxy)phenyl]-3-phenylpyrazoline-1-carboxamide.

EXAMPLE 151

N-[4-(4-Chlorophenoxy)phenyl]-4-(2,2-difluoro-1,3-benzodioxol-5-yl)-3-phenylpyrazoline-1-carboxamide.

EXAMPLE 152

4,N-bis(2,2-Difluoro-1,3-benzodioxol-5-yl)-3-phenyl-pyrazoline-1-carboxamide.

EXAMPLE 153

4-(2,2-Difluoro-1,3-benzodioxol-5-yl)-N-(2,3-dihydro-2,2,3,3-tetrafluorobenzofuran-5-yl)-3-phenyl-pyrazoline-1-carboxamide.

EXAMPLE 154

4-(2,2-Difluoro-1,3-benzodioxol-5-yl)-N-(2,3-dihydro-2,3-dimethylbenzofuran-5-yl)-3-phenylpyrazoline-1-carboxamide.

EXAMPLE 155

4-(2,2-Difluoro-1,3-benzodioxol-5-yl)-N-[4-(4-difluoromethoxyphenoxy)phenyl]-3-(4-difluoromethoxyphenyl)-pyrazoline-1-carboxamide.

EXAMPLE 156

N-[4-(4-Chlorophenoxy)phenyl]-4-(2,2-difluoro-1,3-benzodioxol-5-yl)-3-(4-difluoromethoxyphenyl)pyrazoline-1-carboxamide.

EXAMPLE 157

4,N-bis(2,2-Difluoro-1,3-benzodioxol-5-yl)-3-(4-difluoromethoxyphenyl)pyrazoline-1-carboxamide.

EXAMPLE 158

4-(2,2-Difluoro-1,3-benzodioxol-5-yl)-3-(4-difluoromethoxyphenyl)-N-(2,3-dihydro-2,2,3,3-tetrafluorobenzofuran-5-yl)pyrazoline-1-carboxamide.

EXAMPLE 159

4-(2,2-Difluoro-1,3-benzodioxol-5-yl)-3-(4-difluoromethoxyphenyl)-N-(2,3-dihydro-2,2-dimethylbenzofuran-5-yl)pyrazoline-1-carboxamide.

EXAMPLE 160

4-(1,4-Benzodioxan-6-yl)-3-(4-chlorophenyl)-N-[4-(4-difluoromethoxyphenoxy)phenyl]pyrazoline-1-carboxamide.

EXAMPLE 161

4-(1,4-Benzodioxan-6-yl)-N-[4-(4-chlorophenoxy)phenyl]3-(4-chlorophenyl)pyrazoline-1-carboxamide.

EXAMPLE 162

4-(1,4-Benzodioxan-6-yl)-3-(4-chlorophenyl)-N-(2,2-difluoro-1,3-benzodioxol-5-yl)pyrazoline-1-carboxamide.

EXAMPLE 163

4-(1,4-Benzodioxan-6-yl)-3-(4-chlorophenyl)-N-(2,3-dihydro-2,2,3,3-tetrafluorobenzofuran-5-yl)pyrazoline-1-carboxamide.

EXAMPLE 164

4-(1,4-Benzodioxan-6-yl)-3-(4-chlorophenyl)-N-(2,3-dihydro-2,2-dimethylbenzofuran-5-yl)pyrazoline-1-carboxamide.

EXAMPLE 165

4-(1,4-Benzodioxan-6-yl)-N-[4-(4-difluoromethoxyphenoxy)phenyl]-3-(4-difluoromethoxyphenyl)pyrazoline-1-carboxamide.

EXAMPLE 166

4-(1,4-Benzodioxan-6-yl)-N-[4-(4-chlorophenoxy)phenyl]-3-(4-difluoromethoxyphenyl)pyrazoline-1-carboxamide.

EXAMPLE 167

4-(1,4-Benzodioxan-6-yl)-N-(2,2-difluoro-1,3-benzodioxol-5-yl)-3-(4-difluoromethoxyphenyl)pyrazoline-1-carboxamide.

EXAMPLE 168

4-(1,4-Benzodioxan-6-yl)-3-(4-difluoromethoxyphenyl)-N-(2,3-dihydro-2,2,3,3-tetrafluorobenzofuran-5-yl)pyrazoline-1-carboxamide.

EXAMPLE 169

4-(1,4-Benzodioxan-6-yl)-3-(4-difluoromethoxyphenyl)-N-(2,3-dihydro-2,2-dimethylbenzofuran-5-yl)pyrazoline-1-carboxamide.

EXAMPLE 170

4-(1,4-Benzodioxan-6-yl)-N-[4-(4-difluoromethoxyphenoxy)phenyl]-3-phenylpyrazoline-1-carboxamide.

EXAMPLE 171

4-(1,4-Benzodioxan-6-yl)-N-[4-(4-chlorophenoxy)phenyl]-3-phenylpyrazoline-1-carboxamide.

EXAMPLE 172

4-(1,4-Benzodioxan-6-yl)-N-(2,2-difluoro-1,3-benzodioxol-5-yl)-3-phenylpyrazoline-1-carboxamide.

EXAMPLE 173

4-(1,4-Benzodioxan-6-yl)-N-(2,3-dihydro-2,2,3,3-tetrafluorobenzofuran-5-yl)-3-phenylpyrazoline-1-carboxamide.

EXAMPLE 174

4-(1,4-Benzodioxan-6-yl)-N-(2,3-dihydro-2,2-dimethylbenzofuran-5-yl)-3-phenylpyrazoline-1-carboxamide.

EXAMPLE 175

3-(1,3-Benzodioxol-5-yl)-N-[4-(4-difluoromethoxyphenoxy)phenyl]-4-(4-fluorophenyl)-N-methylpyrazoline-1-carboxamide.

EXAMPLE 176

3-(1,3-Benzodioxol-5-yl)-N-[4-(4-chlorophenoxy)phenyl]-4-(4-fluorophenyl)pyrazoline-1-carboxamide.

EXAMPLE 177

3-(1,3-Benzodioxol-5-yl)-N-(2,2-difluoro-1,3-benzodioxol-5-yl)-4-(4-fluorophenyl)pyrazoline-1-carboxamide.

EXAMPLE 178

3-(1,3-Benzodioxol-5-yl)-4-(4-fluorophenyl)-N-(2,3-dihydro-2,2,3,3-tetrafluorobenzofuran-5-yl)pyrazoline-1-carboxamide.

EXAMPLE 179

3-(1,3-Benzodioxol-5-yl)-4-(4-fluorophenyl)-N-(2,3-dihydro-2,2-dimethylbenzofuran-5-yl)pyrazoline-1-carboxamide.

EXAMPLE 180

3-(2,2-Difluoro-1,3-benzodioxol-5-yl)-N-[4-(4-difluoromethoxyphenoxy)phenyl]-4-(4-fluorophenyl)-pyrazoline-1-carboxamide.

EXAMPLE 181

N-[4-(4-Chlorophenoxy)phenyl]-3-(2,2-difluoro-1,3-benzodioxol-5-yl)-4-(4-fluorophenyl)-N-methylpyrazoline-1-carboxamide.

EXAMPLE 182

3,N-bis(2,2-Difluoro-1,3-benzodioxol-5-yl)-4-(4-fluorophenyl)pyrazoline-1-carboxamide.

EXAMPLE 183

3-(2,2-Difluoro-1,3-benzodioxol-5-yl)-4-(4-fluorophenyl)-N-(2,3-dihydro-2,2,3,3-tetrafluorobenzofuran-5-yl)pyrazoline-1-carboxamide.

EXAMPLE 184

3-(2,2-Difluoro-1,3-benzodioxol-5-yl)-4-(4-fluorophenyl)-N-(2,3-dihydro-2,2-dimethylbenzofuran-5-yl)pyrazoline-1-carboxamide.

EXAMPLE 185

3-(1,4-Benzodioxan-6-yl)-N-[4-(4-difluoromethoxyphenoxy)phenyl]-4-phenylpyrazoline-1-carboxamide.

EXAMPLE 186

3-(1,4-Benzodioxan-6-yl)-N-[4-(4-chlorophenoxy)phenyl]-4-phenylpyrazoline-1-carboxamide.

EXAMPLE 187

3-(1,4-Benzodioxan-6-yl)-N-(2,2-difluoro-1,3-benzodioxol-5-yl)-N-methyl-4-phenylpyrazoline-1-carboxamide.

EXAMPLE 188

3-(1,4-Benzodioxan-6-yl)-N-(2,3-dihydro-2,2,3,3-tetrafluorobenzofuran-5-yl)-4-phenylpyrazoline-1-carboxamide.

EXAMPLE 189

3-(1,4-Benzodioxan-6-yl)-N-(2,3-dihydro-2,2-dimethylbenzofuran-5-yl)-4-phenylpyrazoline-1-carboxamide.

EXAMPLE 190

N-[4-(4-Difluoromethoxyphenoxy)phenyl]-3-(2,3-dihydro-2,2-dimethylbenzofuran-5-yl)-4-phenylpyrazoline-1-carboxamide.

EXAMPLE 191

N-[4-(4-Chlorophenoxy)phenyl]-3-(2,3-dihydro-2,2-dimethylbenzofuran-5-yl)-4-phenylpyrazoline-1-carboxamide.

EXAMPLE 192

N-(2,2-Difluoro-1,3-benzodioxol-5-yl)-3-(2,3-dihydro-2,2-dimethylbenzofuran-5-yl)-4-phenylpyrazoline-1-carboxamide.

EXAMPLE 193

N-(2,3-Dihydro-2,2,3,3-tetrafluorobenzofuran-5-yl)-3-(2,3-dihydro-2,2-dimethylbenzofuran-5-yl)-N-methyl-4-phenylpyrazoline-1-carboxamide.

EXAMPLE 194

3,N-bis(2,3-Dihydro-2,2-dimethylbenzofuran-5-yl)-4-phenylpyrazoline-1-carboxamide.

EXAMPLE 195

N-[4-(4-Difluoromethoxyphenoxy)phenyl]-4-(4-fluorophenyl)-3-(4-methylphenyl)pyrazoline-1-carboxamide.

EXAMPLE 196

N-[4-(4-Chlorophenoxy)phenyl]-4-(4-fluorophenyl)-3-(4-methylphenyl)pyrazoline-1-carboxamide.

EXAMPLE 197

N-(2,2-Difluoro-1,3-benzodioxol-5-yl)-4-(4-fluorophenyl)-3-(4-methylphenyl)pyrazoline-1-carboxamide.

EXAMPLE 198

4-(4-Fluorophenyl)-N-(2,3-dihydro-2,2,3,3-tetrafluorobenzofuran-5-yl)-3-(4-methylphenyl)pyrazoline-1-carboxamide.

EXAMPLE 199

4-(4-Fluorophenyl)-N-(2,3-dihydro-2,2-dimethylbenzofuran-5-yl)-N-methyl-3-(4-methylphenyl)pyrazoline-1-carboxamide.

EXAMPLE 200

N-[4-(4-Difluoromethoxyphenoxy)phenyl]-4-(3-fluorophenyl)-N-methyl-3-(4-methylphenyl)pyrazoline-1-carboxamide.

EXAMPLE 201

N-[4-(4-Chlorophenoxy)phenyl]-4-(3-fluorophenyl)-3-(4-methylphenyl)pyrazoline-1-carboxamide.

EXAMPLE 202

N-(2,2-Difluoro-1,3-benzodioxol-5-yl)-4-(3-fluorophenyl)-3-(4-methylphenyl)pyrazoline-1-carboxamide.

EXAMPLE 203

4-(3-Fluorophenyl)-N-(2,3-dihydro-2,2,3,3-tetrafluorobenzofuran-5-yl)-3-(4-methylphenyl)pyrazoline-1-carboxamide.

EXAMPLE 204

4-(3-Fluorophenyl)-N-(2,3-dihydro-2,2-dimethylbenzofuran-5-yl)-3-(4-methylphenyl)pyrazoline-1-carboxamide.

EXAMPLE 205

N-[4-(4-Difluoromethoxyphenoxy)phenyl]-4-(2-fluorophenyl)-3-(4-methylphenyl)pyrazoline-1-carboxamide.

EXAMPLE 206

N-[4-(4-Chlorophenoxy)phenyl]-4-(3-fluorophenyl)-N-methyl-3-(4-methylphenyl)pyrazoline-1-carboxamide.

EXAMPLE 207

N-(2,2-Difluoro-1,3-benzodioxol-5-yl)-4-(2-fluorophenyl)-3-(4-methylphenyl)pyrazoline-1-carboxamide.

EXAMPLE 208

4-(2-Fluorophenyl)-N-(2,3-dihydro-2,2,3,3-tetrafluorobenzofuran-5-yl)-3-(4-methylphenyl)pyrazoline-1-carboxamide.

EXAMPLE 209

4-(2-Fluorophenyl)-N-(2,3-dihydro-2,2-dimethylbenzofuran-5-yl)-3-(4-methylphenyl)pyrazoline-1-carboxamide.

EXAMPLE 210

N-[4-(4-Difluoromethoxyphenoxy)phenyl]-3-(3-fluorophenyl)-4-(4-fluorophenyl)pyrazoline-1-carboxamide.

EXAMPLE 211

N-[4-(4-Chlorophenoxy)phenyl]-3-(3-fluorophenyl)-4-(4-fluorophenyl)pyrazoline-1-carboxamide.

EXAMPLE 212

N-(2,2-Difluoro-1,3-benzodioxol-5-yl)-3-(3-fluorophenyl-4-(4-fluorophenyl)-N-methylpyrazoline-1-carboxamide.

EXAMPLE 213

3-(3-Fluorophenyl)-4-(4-fluorophenyl)-N-(2,3-dihydro-2,2,3,3-tetrafluorobenzofuran-5-yl)pyrazoline-1-carboxamide.

EXAMPLE 214

3-(3-Fluorophenyl)-4-(4-fluorophenyl)-N-(2,3-dihydro-2,2-dimethylbenzofuran-5-yl)pyrazoline-1-carboxamide.

EXAMPLE 215

N-[4-(4-Difluoromethoxyphenoxy)phenyl]-3-(2-fluorophenyl)-4-(4-fluorophenyl)pyrazoline-1-carboxamide.

EXAMPLE 216

N-[4-(4-Chlorophenoxy)phenyl]-3-(2-fluorophenyl)-4-(4-fluorophenyl)pyrazoline-1-carboxamide.

EXAMPLE 217

N-(2,2-Difluoro-1,3-benzodioxol-5-yl)-3-(2-fluorophenyl)-4-(4-fluorophenyl)pyrazoline-1-carboxamide.

EXAMPLE 218

3-(2-Fluorophenyl)-4-(4-fluorophenyl)-N-(2,3-dihydro-2,2,3,3-tetrafluorobenzofuran-5-yl)-N-methylpyrazoline-1-carboxamide.

EXAMPLE 219

3-(2-Fluorophenyl)-4-(4-fluorophenyl)-N-(2,3-dihydro-2,2-dimethylbenzofuran-5-yl)pyrazoline-1-carboxamide.

EXAMPLE 220

3,4-bis(4-Fluorophenyl)-N-(2,3-dihydro-2,2,3,3,7-pentafluorobenzofuran-5-yl)pyrazoline-1-carboxamide.

EXAMPLE 221

4-(4-Chlorophenyl)-N-(2,3-dihydro-2,2,3,3,7-pentafluorobenzofuran-5-yl)-3-(4-methylphenyl)pyrazoline-1-carboxamide.

EXAMPLE 222

N-(2,3-Dihydro-2,2,3,3,7-pentafluorobenzofuran-5-yl)-3,4-diphenylpyrazoline-1-carboxamide.

EXAMPLE 223

3-(4-Difluoromethoxyphenyl)-N-(2,3-dihydro-2,2,3,3,7-pentafluorobenzofuran-5-yl)-4-phenylpyrazoline-1-carboxamide.

EXAMPLE 224

3-(4-Chlorophenyl)-N-(2,3-dihydro-2,2,3,3,7-pentafluorobenzofuran-5-yl)-4-phenylpyrazoline-1-carboxamide.

EXAMPLE 225

3,4-bis(4-Fluorophenyl)-N-(2,2,6-trimethyl-1,3-benzodioxol-5-yl)pyrazoline-1-carboxamide.

EXAMPLE 226

4-(4-Chlorophenyl)-N-(2,2,6-trimethyl-1,3-benzodioxol-5-yl)-3-(4-methylphenyl)pyrazoline-1-carboxamide.

EXAMPLE 227

N-(2,2,6-Trimethyl-1,3-benzodioxol-5-yl)-3,4-diphenylpyrazoline-1-carboxamide.

EXAMPLE 228

3-(4-Difluoromethoxyphenyl)-N-(2,2,6-trimethyl-1,3-benzodioxol-5-yl)-4-phenylpyrazoline-1-carboxamide.

EXAMPLE 229

3-(4-Chlorophenyl)-N-(2,2,6-trimethyl-1,3-benzodioxol-5-yl)-4-phenylpyrazoline-1-carboxamide.

EXAMPLE 230

3,4-bis(4-Fluorophenyl)-N-(7-methoxy-2,2-dimethyl-1,3-benzodioxol-5-yl)pyrazoline-1-carboxamide.

EXAMPLE 231

4-(Chlorophenyl)-N-(7-methoxy-2,2-dimethyl-1,3-benzodioxol-5-yl)-3-(4-methylphenyl)pyrazoline-1-carboxamide.

EXAMPLE 232

N-(7-Methoxy-2,2-dimethyl-1,3-benzodioxol-5-yl)-3,4-diphenylpyrazoline-1-carboxamide.

EXAMPLE 233

3-(4-Difluoromethoxyphenyl)-N-(7-methoxy-2,2-dimethyl-1,3-benzodioxol-5-yl)-4-phenylpyrazoline-1-carboxamide.

EXAMPLE 234

3-(4-Chlorophenyl)-N-(7-methoxy-2,2-dimethyl-1,3-benzodioxol-5-yl)-4-phenylpyrazoline-1-carboxamide.

EXAMPLE 235

3,4-bis(4-Fluorophenyl)-N-[2,2-dimethyl-7-(1-methylethyl)-1,3-benzodioxol-5-yl]pyrazoline-1-carboxamide.

EXAMPLE 236

4-(4-Chlorophenyl)-N-[2,2-dimethyl-7-(1-methylethyl)-1,3-benzodioxol-5-yl]-3-(4-methylphenyl)pyrazoline-1-carboxamide.

EXAMPLE 237

N-[2,2-Dimethyl-7-(1-methylethyl)-1,3-benzodioxol-5-yl]-3,4-diphenylpyrazoline-1-carboxamide.

EXAMPLE 238

3-(4-Difluoromethoxyphenyl)-N-[2,2-dimethyl-7-(1-methylethyl)-1,3-benzodioxol-5-yl]-4-phenylpyrazoline-1-carboxamide.

EXAMPLE 239

3-(4-Chlorophenyl)-N-[2,2-dimethyl-7-(1-methylethyl)-1,3-benzodioxol-5-yl]-4-phenylpyrazoline-1-carboxamide.

EXAMPLE 240

3,4-bis(4-Fluorophenyl)-N-(2,3-dihydro-7-ethyl-2,2,3,3-tetrafluorobenzofuran-5-yl)pyrazoline-1-carboxamide, mp 144–148. 8.50 ppm.

EXAMPLE 241

4-(4-Chlorophenyl)-N-(2,3-dihydro-7-ethyl-2,2,3,3-tetrafluorobenzofuran-5-yl)-3-(4-methylphenyl)pyrazoline-1-carboxamide.

EXAMPLE 242

N-(2,3-Dihydro-7-ethyl-2,2,3,3-tetrafluorobenzofuran-5-yl)-3,4-diphenylpyrazoline-1-carboxamide.

EXAMPLE 243

3-(4-Difluoromethoxyphenyl)-N-(2,3-dihydro-7-ethyl-2,2,3,3-tetrafluorobenzofuran-5-yl)-4-phenylpyrazoline-1-carboxamide.

EXAMPLE 244

3-(4-Chlorophenyl)-N-(2,3-dihydro-7-ethyl-2,2,3,3-tetrafluorobenzofuran-5-yl)-4-phenylpyrazoline-1-carboxamide.

EXAMPLE 245

3-(4-Chlorophenyl)-N-[4-(4-methylsulfonylphenoxy)phenyl]-4-phenylpyrazoline-1-carboxamide.

EXAMPLE 246

3,4-bis(4-Fluorophenyl)-N-[4-(4-methylsulfonylphenoxy)phenyl]pyrazoline-1-carboxamide, mp 177–178. 8.16 ppm.

EXAMPLE 247

3-(4-Difluoromethoxyphenyl)-N-[4-(4-methylsulfonylphenoxy)phenyl]-4-phenylpyrazoline-1-carboxamide.

EXAMPLE 248

3-(4-Chlorophenyl)-4-(4-fluorophenyl)-N-[4-(4-methylsulfonylphenoxy)phenyl]pyrazoline-1-carboxamide.

EXAMPLE 249

N-[4-(4-Methylsulfonylphenoxy)phenyl]-3,4-diphenylpyrazoline-1-carboxamide.

EXAMPLE 250

3,4-bis(4-Fluorophenyl)-N-(2,3-dihydro-7-difluoromethoxy-2,2-dimethylbenzofuran-5-yl)pyrazoline-1-carboxamide, mp 146–150. 8.00 ppm.

EXAMPLE 251

4-(4-Chlorophenyl)-N-(2,3-dihydro-7-difluoromethoxy-2,2-dimethylbenzofuran-5-yl)-3-(4-methylphenyl)pyrazoline-1-carboxamide.

EXAMPLE 252

N-(2,3-Dihydro-7-difluoromethoxy-2,2-dimethylbenzofuran-5-yl)-3,4-diphenylpyrazoline-1-carboxamide.

EXAMPLE 253

3-(4-Difluoromethoxyphenyl)-N-(2,3-dihydro-7-difluoromethoxy-2,2-dimethylbenzofuran-5-yl)-4-phenylpyrazoline-1-carboxamide.

EXAMPLE 254

3-(4-Chlorophenyl)-N-(2,3-dihydro-7-difluoromethoxy-2,2-dimethylbenzofuran-5-yl)-4-phenylpyrazoline-1-carboxamide.

EXAMPLE 255

N-(7-Chloromethyl-2,2-dimethyl-1,3-benzodioxol-5-yl)-3,4-bis(4-fluorophenyl)pyrazoline-1-carboxamide.

EXAMPLE 256

N-(7-Chloromethyl-2,2-dimethyl-1,3-benzodioxol-5-yl)-4-(4-chlorophenyl)-3-(4-methylphenyl)pyrazoline-1-carboxamide.

EXAMPLE 257

N-(7-Chloromethyl-2,2-dimethyl-1,3-benzodioxol-5-yl)-3,4-diphenylpyrazoline-1-carboxamide.

EXAMPLE 258

N-(7-Chloromethyl-2,2-dimethyl-1,3-benzodioxol-5-yl)-3-(4-difluoromethoxyphenyl)-4-phenylpyrazoline-1-carboxamide.

EXAMPLE 259

N-(7-Chloromethyl-2,2-dimethyl-1,3-benzodioxol-5-yl)-3-(4-chlorophenyl)-4-phenylpyrazoline-1-carboxamide.

EXAMPLE 260

N-(2,3-Dihydro-2,2-dimethylbenzofuran-5-yl)-3-[7-(1-methylethyl)-2,2-dimethyl-1,3-benzodioxol-5-yl]-4-phenylpyrazoline-1-carboxamide.

EXAMPLE 261

N-(2,3-Dihydro-2,2-dimethylbenzofuran-5-yl)-3-(7-methoxy-2,2-dimethyl-1,3-benzodioxol-5-yl)-4-phenylpyrazoline-1-carboxamide.

EXAMPLE 262

N-(2,3-Dihydro-2,2-dimethylbenzofuran-5-yl)-3-(7-fluoro-2,2-dimethyl-1,3-benzodioxol-5-yl)-4-phenylpyrazoline-1-carboxamide.

EXAMPLE 263

N-(2,3-Dihydro-2,2-dimethylbenzofuran-5-yl)-3-(7-difluoromethoxy-2,2-dimethyl-1,3-benzodioxol-5-yl)-4-phenylpyrazoline-1-carboxamide.

EXAMPLE 264

N-(2,2-Difluoro-1,3-benzodioxol-5-yl)-3-(4-fluorophenyl)-4-(2,3-dihydro-2,2-dimethylbenzofuran-5-yl)pyrazoline-1-carboxamide.

EXAMPLE 265

N-(2,2-Difluoro-1,3-benzodioxol-5-yl)-3-(4-fluorophenyl)-4-(2,3-dihydro-2,2,3,3-tetrafluorobenzofuran-5-yl)pyrazoline-1-carboxamide.

EXAMPLE 266

N-[3-(4-Trifluoromethylphenoxy)phenyl]-3,4-bis(4-fluorophenyl)pyrazoline-1-carboxamide.

EXAMPLE 267

N-[3-(4-Fluorophenoxy)phenyl]-3,4-bis(4-fluorophenyl)-pyrazoline-1-carboxamide.

EXAMPLE 268

N-[3-(4-Difluoromethoxyphenoxy)phenyl]-3,4-bis(4-fluorophenyl)pyrazoline-1-carboxamide.

EXAMPLE 269

3,4-bis(4-Fluorophenyl)-N-[3-(4-methylphenoxy)-phenyl]pyrazoline-1-carboxamide.

EXAMPLE 270

3-(7-Chloromethyl-2,2-dimethyl-1,3-benzodioxol-5-yl)-4,N-bis(4-fluorophenyl)pyrazoline-1-carboxamide.

EXAMPLE 271

N-(2,3-Dihydro-2,2-dimethylbenzofuran-5-yl)-4-[7-(1-methylethyl)-2,2-dimethyl-1,3-benzodioxol-5-yl]-3-phenylpyrazoline-1-carboxamide.

EXAMPLE 272

N-(2,3-Dihydro-2,2-dimethylbenzofuran-5-yl)-4-(7-methoxy-2,2-dimethyl-1,3-benzodioxol-5-yl)-3-phenyl-pyrazoline-1-carboxamide.

EXAMPLE 273

N-(2,3-Dihydro-2,2-dimethylbenzofuran-5-yl)-4-(7-fluoro-2,2-dimethyl-1,3-benzodioxol-5-yl)-3-phenyl-pyrazoline-1-carboxamide.

EXAMPLE 274

N-(2,3-Dihydro-2,2-dimethylbenzofuran-5-yl)-4-(7-difluoromethoxy-2,2-dimethyl-1,3-benzodioxol-5-yl)-3-phenylpyrazoline-1-carboxamide.

EXAMPLE 275

4-(7-Chloromethyl-2,2-dimethyl-1,3-benzodioxol-5-yl)-3,N-bis(4-fluorophenyl)pyrazoline-1-carboxamide.

EXAMPLE 276

3,4-bis(4-Fluorophenyl)-N-(4-phenoxyphenyl)-pyrazoline-1-carbothioamide, mp 166–168. 9.05 ppm.

EXAMPLE 277

3,4-bis(4-Fluorophenyl)-N-[4-(4-methylphenoxy)-phenyl]pyrazoline-1-carboxamide. 8.0 ppm.

EXAMPLE 278

3,4-bis(4-Fluorophenyl)-N-[4-[4-(1-methylethyl)-phenoxy]phenyl]pyrazoline-1-carboxamide, mp 183–185. 8.0 ppm.

EXAMPLE 279

3,4-bis(4-Fluorophenyl)-N-[4-(4-phenylphenoxy)-phenyl]pyrazoline-1-carboxamide, mp 167.5–169. 8.06 ppm.

EXAMPLE 280

3-(4-Chlorophenyl)-N-[4-(4-cyanophenoxy)phenyl]-4-(4-fluorophenyl)pyrazoline-1-carboxamide, mp 141–143. 8.13 ppm.

EXAMPLE 281

N-[4-(4-Chlorophenoxy)phenyl]-3-(4-fluorophenyl)-4-phenylpyrazoline-1-carboxamide, mp 158–161. 8.56 ppm. (CDCl$_3$/DMSO-d$_6$).

EXAMPLE 282

N-[4-(4-Bromophenoxy)phenyl]-3-(4-chlorophenyl)-4-phenylpyrazoline-1-carboxamide, mp 164–166. 8.06 ppm.

EXAMPLE 283

N-[4-(4-Bromophenoxy)phenyl]-3,4-bis(4-fluorophenyl)pyrazoline-1-carboxamide, mp 186–188. 8.03 ppm.

EXAMPLE 284

N-[4-(4-Bromophenoxy)phenyl]-3-(4-chlorophenyl)-4-(4-fluorophenyl)pyrazoline-1-carboxamide, mp 158–160. 8.33 ppm (CDCl$_3$/DMSO-d$_6$).

EXAMPLE 285

3,4-bis(4-Fluorophenyl)-N-[4-(4-nitrophenoxy)-phenyl]pyrazoline-1-carboxamide, mp 158–160. 8.26 ppm.

EXAMPLE 286

3-(4-Chlorophenyl)-4-(4-fluorophenyl)-N-[4-(4-nitrophenoxy)phenyl]pyrazoline-1-carboxamide. 8.26 ppm.

EXAMPLE 287

3-(4-Chlorophenyl)-4-(4-fluorophenyl)-N-[4-[4-(N,N-dimethylamine)phenoxy]phenyl]pyrazoline-1-carboxamide, mp 157–158. 8.04 ppm.

EXAMPLE 288

N-[4-(4-Benzoylphenoxy)phenyl]-3,4-bis(4-fluorophenyl)pyrazoline-1-carboxamide. 8.13 ppm.

EXAMPLE 289

N-[4-(4-Benzoylphenoxy)phenyl]-3-(4-chlorophenyl)-4-(4-fluorophenyl)pyrazoline-1-carboxamide. 8.16 ppm.

EXAMPLE 290

N-[4-(4-Benzoylphenoxy)phenyl]-3-(4-chlorophenyl)-4-phenylpyrazoline-1-carboxamide. 8.03 ppm.

EXAMPLE 291

3-(4-Chlorophenyl)-N-[4-(4-hexoxyphenoxy)phenyl]-4-phenylpyrazoline-1-carboxamide, mp 105–107. 8.1 ppm.

EXAMPLE 292

3-(4-Chlorophenyl)-4-(4-fluorophenyl)-N-[4-(4-hexoxyphenoxy)phenyl]pyrazoline-1-carboxamide, mp 108–110. 8.1 ppm.

EXAMPLE 293

3,4-bis(4-Fluorophenyl)-N-[4-(4-hexoxyphenoxy)-phenyl]pyrazoline-1-carboxamide, mp 101–103. 8.1 ppm.

EXAMPLE 294

3,4-bis(4-Fluorophenyl)-N-[4-(4-phenoxyphenoxy)-phenyl]pyrazoline-1-carboxamide, mp 119–121. 8.06 ppm.

EXAMPLE 295

N-[4-(4-Benzoyloxyphenoxy)phenyl]-3,4-bis(4-fluorophenyl)pyrazoline-1-carboxamide, mp 168–170. 8.33 ppm.

EXAMPLE 296

N-[4-(4-Difluoromethoxyphenoxy)phenyl]-3,4-bis(4-fluorophenyl)pyrazoline-1-carboxamide, mp 170–172.

EXAMPLE 297

3-(4-Chlorophenyl)-N-[4-(4-difluoromethoxyphenoxy)phenyl]-4-(4-fluorophenyl)pyrazoline-1-carboxamide, mp 141–143. 8.43 ppm.

EXAMPLE 298

N-[4-(3,4-Dichlorophenoxy)phenyl]-3-(4-chlorophenyl)-4-phenylpyrazoline-1-carboxamide, mp 160–165. 8.13 ppm.

EXAMPLE 299

N-[4-(3,4-Dichlorophenoxy)phenyl]-3,4-bis(4-chlorophenyl)pyrazoline-1-carboxamide, mp 149–154. 8.10 ppm.

EXAMPLE 300

3-(4-Chlorophenyl)-N-[4-(2,3,5,6-tetrafluorophenoxy)phenyl]-4-phenylpyrazoline-1-carboxamide, mp 203–205. 8.06 ppm.

EXAMPLE 301

N-[4-(2,3,5,6-Tetrafluorophenoxy)phenyl]-3,4-bis(4-fluorophenyl)pyrazoline-1-carboxamide, mp 160–162. 8.60 ppm.

EXAMPLE 302

3-(4-Chlorophenyl)-N-[4-(2,3,5,6-tetrafluorophenoxy)phenyl]-4-(4-fluorophenyl)pyrazoline-1-carboxamide, mp 171–173. 8.0 ppm.

EXAMPLE 303

3-(4-Chlorophenyl)-N-(indan-5-yl)-4-phenylpyrazoline-1-carboxamide, mp 163–167. 8.06 ppm.

EXAMPLE 304

3-(4-Difluoromethoxyphenyl)-N-(indan-5-yl)-4-phenylpyrazoline-1-carboxamide, mp 149–154. 8.03 ppm.

EXAMPLE 305

3,4-bis(4-Chlorophenyl)-N-(indan-5-yl)pyrazoline-1-carboxamide, mp 222–226. 8.03 ppm (CDCl$_3$/DMSO-d$_6$).

EXAMPLE 306

3,4-bis(4-Fluorophenyl)-N-(chroman-6-yl)pyrazoline-1-carboxamide, mp 182–185. 7.96 ppm.

EXAMPLE 307

3-(4-Chlorophenyl)-N-(2,2-dimethylchroman-6-yl)pyrazoline-1-carboxamide, mp 174–176. 7.93 ppm.

EXAMPLE 308

3-(4-Chlorophenyl)-4-(4-fluorophenyl)-N-(2,2-dimethylchroman-6-yl)pyrazoline-1-carboxamide, mp 187–188.5. 7.93 ppm.

EXAMPLE 309

3-(4-Difluoromethoxyphenyl)-N-(2,2-dimethylchroman-6yl)-4-phenylpyrazoline-1-carboxamide, mp 200–201.5. 7.9 ppm.

EXAMPLE 310

3,4-bis(4-Chlorophenyl)-N-(2,2-dimethylchroman-6-yl)pyrazoline-1-carboxamide, mp 160–163. 7.9 ppm.

EXAMPLE 311

3-(4-Chlorophenyl)-4-(3,4-dichlorophenyl)-N-(2,3-dihydro-2,2-dimethylbenzofuran-5-yl)pyrazoline-1-carboxamide, mp 164–168. 8.03 ppm.

EXAMPLE 312

4-(4-Chlorophenyl)-N-(2,3-dihydro-2,2,3,3-tetrafluorobenzofuran-5-yl)-3-phenylpyrazoline-1-carboxamide, mp 159–163. 8.25 ppm.

EXAMPLE 313

N-(2,3-Dihydro-2,2,3,3-tetrafluorobenzofuran-5-yl)-3-(4-fluorophenyl)-4-phenylpyrazoline-1-carboxamide, mp 143–147. 8.03 ppm.

EXAMPLE 314

N-(2,3-Dihydro-2,2,3,3-tetrafluorobenzofuran-5-yl)-4-(4-fluorophenyl)-3-phenylpyrazoline-1-carboxamide, mp 169–173. 8.26 ppm.

EXAMPLE 315

4-(4-Chlorophenyl)-N-(2,3-dihydro-2,2,3,3-tetrafluorobenzofuran-5-yl)-3-(4-fluorophenyl)pyrazoline-1-carboxamide, mp 153–158. 8.23 ppm.

EXAMPLE 316

N-(2,3-Dihydro-2,2,3,3-tetrafluorobenzofuran-5-yl)-3,4-bis(4-fluorophenyl)pyrazoline-1-carboxamide, mp 156–160. 8.23 ppm.

EXAMPLE 317

N-(2,3-Dihydro-7-chloro-2,2,3,3-tetrafluorobenzofuran-5yl)-3,4-bis(4-fluorophenyl)pyrazoline-1-carboxamide, mp 185–189. 8.66 ppm.

EXAMPLE 318

4-(4-Chlorophenyl)-N-(2,3-dihydro-2,2,3,3-tetrafluorobenzofuran-5-yl)-3-(4-difluoromethoxyphenyl)-pyrazoline-1-carboxamide, mp 89–93. 8.20 ppm.

EXAMPLE 319

N-(2,3-Dihydro-2,2,3,3-tetrafluorobenzofuran-5-yl)-3-(4-difluoromethoxyphenyl)-4-phenylpyrazoline-1-carboxamide.

EXAMPLE 320

N-(2,3-Dihydro-2,2,3,3-tetrafluorobenzofuran-5-yl)-3-(4-difluoromethoxyphenyl)-N-propyl-4-phenyl-pyrazoline-1-carboxamide.

EXAMPLE 321

3-(4-Chlorophenyl)-N-(2,2-diethyl-1,3-benzodioxol-5-yl)-4-(4-fluorophenyl)pyrazoline-1-carboxamide, mp 169–171. 7.93 ppm.

EXAMPLE 322

N-(2,2-Diethyl-1,3-benzodioxol-5-yl -3,4-bis(4-fluorophenyl)pyrazoline-1-carboxamide, mp 160–163. 7.93 ppm.

EXAMPLE 323

4-(4-Chlorophenyl)-N-(2,2-difluoro-1,3-benzodioxol-5-yl)-3-henylpyrazoline-1-carboxamide, mp 139–144. 8.1 ppm.

EXAMPLE 324

4-(4-Chlorophenyl)-N-(2,2-difluoro-1,3-benzodioxol-5-yl)-3-(4-fluorophenyl)pyrazoline-1-carboxamide, mp 109–113. 7.93 ppm.

EXAMPLE 325

N-(2,2-Difluoro-1,3-benzodioxol-5-yl)-3-(4-fluorophenyl)-4-phenylpyrazoline-1-carboxamide, mp 214–218. 8.96 ppm (CDCl$_3$/DMSO-d$_6$).

EXAMPLE 326

N-(2,2-Difluoro-1,3-benzodioxol-5-yl)-4-(4-fluorophenyl)-3-phenylpyrazoline-1-carboxamide, mp 201–204. 8.63 ppm (CDCl$_3$/DMSO-d$_6$).

EXAMPLE 327

3,4-bis(4-chlorophenyl)-N-(2,2,3-trifluoro-1,4-benzodioxan-6-yl)pyrazoline-1-carboxamide, mp 108–111. 8.03 ppm.

EXAMPLE 328

3-(4-Chlorophenyl)-N-(2,2,3-trifluoro-1,4-benzodioxan-6-yl)-4-phenylpyrazoline-1-carboxamide, mp 177–180. 9.3 ppm (CDCl$_3$/DMSO-d$_6$).

EXAMPLE 329

N-(2,2,3-Trifluoro-1,4-benzodioxan-6-yl)-3-(4-difluoromethoxyphenyl)-4-phenylpyrazoline-1-carboxamide, mp 67–70. 8.06 ppm.

EXAMPLE 330

N-(2,2,3-Trifluoro-1,4-benzodioxan-6-yl)-3,4-bis(4-fluorophenyl) pyrazoline-1-carboxamide, mp 211–214. 8.06 ppm.

EXAMPLE 331

N-(3-Chloro-2,2,3-trifluoro-1,4-benzodioxan-6-yl)-3,4-bis(4-fluorophenyl)pyrazoline-1-carboxamide, mp 88–91. 8.16 ppm.

EXAMPLE 332

N-(3-Chloro-2,2,3-trifluoro-1,4-benzodioxan-6-yl)-3-(4-difluoromethoxyphenyl)-4-phenylpyrazoline-1-carboxamide, mp 68–71. 8.13 ppm.

EXAMPLE 333

N-(3-Chloro-2,2,3-trifluoro-1,4-benzodioxan-6-yl)-3,-bis(4-chlorophenyl)pyrazoline-1-carboxamide, mp 155–158. 8.1 ppm.

EXAMPLE 334

N-(3-Chloro-2,2,3-trifluoro-1,4-benzodioxan-6-yl)-3-(4-chlorophenyl)-4-phenylpyrazoline-1-carboxamide, mp 111–113. 8.17 ppm.

EXAMPLE 335

N-(2,2-Difluoro-1,3-benzodioxol-5-yl)-4-(2-fluorophenyl)-3-phenylpyrazoline-1-carboxamide, mp 175–177. 9.30 ppm (DMSO-d$_6$).

EXAMPLE 336

N-(2,3-Dihydro-2,2,3,3-tetrafluorobenzofuran-5-yl)-4-(2-fluorophenyl)-3-phenylpyrazoline-1-carboxamide, mp 213–215. 8.36 ppm.

In the normal use of the insecticidal pyrazolines of the present invention, the pyrazolines usually will not be employed free from admixture or dilution, but ordinarily will be used in a suitable formulated composition compatible with the method of application and comprising an insecticidally effective amount of pyrazoline. The pyrazolines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present pyrazolines may be applied, for example, as sprays, dusts, or granules to the area where pest control is desired, the type of application varying of course with the pest and the environment. Thus, the pyrazolines of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the pyrazolines. The granule particles are relatively large, a diameter of about 400–2500 microns typically. The particles are either impregnated with the pyrazoline from solution or coated with the pyrazoline, adhesive sometimes being employed. Granules generally contain 0.05–10%, preferably 0.5–5%, active ingredient as the insecticidally effective amount.

Dusts are admixtures of the pyrazolines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of pyrazoline, such as 3-(4-chlorophenyl)-N-[4-(4-chlorophenoxy)phenyl]-4-phenylpyrazoline-1-carboxamide, and 99 parts of talc.

The pyrazolines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% pyrazoline, such as 3-(4-chlorophenyl)-N-(2,3-dihydro-2,2-dimethylbenzofuran-5-yl)-4-phenylpyrazoline-1-carboxamide, and 95–50% inert material, which includes surface-active dispersing, emulsifying, and wetting agents, but ever higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium laurylsulfate as wetting agents, 25 parts of 3-(4-chlorophenyl)-N-(2,3-dihydro-2,2-dimethylbenzofuran-5-yl)-4-(4-chlorophenyl)-pyrazoline-1-carboxamide, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the pyrazoline with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentration, such as acetone or other organic solvents.

An insecticidally effective amount of pyrazoline in an insecticidal composition diluted for application is normally in the range of about 0.001% to about 8% by weight. Many variations of spraying and dusting compositions known in the art may be used by substituting the pyrazolines of this invention into compositions known or apparent in the art.

The insecticidal compositions of this invention may be formulated with other active ingredients, including other insecticides, nematicides, acaricides, fungicides, plant growth regulators, fertilizers, etc. In using the compositions to control insects, it is only necessary that an insecticidally effective amount of pyrazoline be applied to the locus where control is desired. Such locus may, e.g., be the insects themselves, plants upon which the insects feed, or the insect habitat. When the locus is soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

The insecticidal activity of the pyrazolines whose preparation is described above was evaluated as follows:

The compounds were tested in foliar applications at various concentrations in aqueous solutions containing 10% acetone and 0.25% octyl phenoxypolyethoxy ethanol. Pinto bean plants were placed on a revolving turntable in a hood, and the test solutions were applied with a sprayer. The test solutions were applied to the upper and lower surfaces of the plant leaves to runoff. The plants were then allowed to dry and were severed at the base of the stem. Each stem was inserted through a paper cup into water. Ten individuals of the appropriate insect species were placed in each cup and the cup covered. The evaluation used southern armyworm (*Spodoptera eridania*), Mexican bean beetle (*Epilachna varivestis*), beet armyworm (*Spodoptera exigua*), and cabbage looper (*Trichoplusia ni*). After 4 days at 26° C. and 50% RH mortality was read. The results of the tests appear in Table 1. Insect mortality was generally less if the tests were read much earlier.

A number of the pyrazolines were also active against southern corn rootworm larvae (*Diabrotica undecimpunctata howardi* Barber) when applied to the soil, and those tested were also very effective on Colorado potato beetle (*Leptinotara decemlineata* Say) and corn earworm (*Heliothis zea* Boddie).

TABLE 1

| Compound | Rate (ppm) | Foliar Evaluation Insects (% Kill) | | | |
|---|---|---|---|---|---|
| | | MBB | SAW | BAW | CL |
| 1 | 500 | 100 | 100 | | |
| 2 | 500 | 100 | 100 | | |
| 3 | 500 | 100 | 100 | | |
| 4 | 500 | 100 | 100 | | |
| 5 | 250 | 100 | 87 | | 100 |
| 6 | 500 | 70 | 65 | | 90 |
| 7 | 500 | 100 | 50 | | 90 |
| 8 | 500 | 100 | 85 | | |
| 9 | 500 | 90 | 70 | | |
| 10 | 500 | 100 | 35 | | |
| 11 | 500 | 85 | 15 | | |
| 12 | 500 | 100 | 100 | | |
| 13 | 500 | 93 | 50 | | 90 |
| 14 | 500 | 100 | 100 | | |
| 15 | 500 | 100 | 90 | | |
| 16 | 500 | 100 | | | |
| 17 | 500 | 100 | 35 | | |
| 18 | 500 | 90 | 55 | | |
| 19 | 500 | 100 | 100 | | |
| 20 | 500 | 80 | 40 | | |
| 21 | 500 | 70 | 15 | | |
| 22 | 500 | 100 | 100 | | |
| 23 | 500 | 40 | 30 | | |
| 24 | 250 | 95 | | | 100 |
| 25 | 500 | 30 | 75 | | |
| 26 | 500 | 80 | 65 | | |
| 27 | 500 | 75 | 95 | | |
| 28 | 500 | 95 | 90 | | |
| 29 | 500 | 10 | 90 | | |
| 30 | 500 | 5 | 64 | | 60 |
| 31 | 500 | 5 | 65 | | 70 |
| 32 | 500 | 100 | 50 | | |
| 33 | 500 | 100 | 80 | | |
| 34 | 500 | 10 | 75 | | |
| 35 | 500 | 100 | 100 | | |
| 36 | 8 | 100 | 98 | 45 | 90 |
| 37 | 32 | 98 | 98 | 97 | 100 |
| 37a | 50 | 100 | 100 | | |
| 37b | 50 | 100 | 100 | | |
| 38 | 500 | 95 | 80 | | |
| 39 | 500 | 100 | 25 | | |

TABLE 1-continued

| Compound | Rate (ppm) | MBB | SAW | BAW | CL |
|---|---|---|---|---|---|
| 40 | 500 | 100 | 100 | | |
| 41 | 128 | 95 | 70 | | |
| 42 | 128 | 95 | 100 | | |
| 43 | 500 | 100 | 100 | | |
| 44 | 500 | 100 | 100 | | |
| 45 | 32 | 100 | 100 | 100 | 100 |
| 46 | 500 | 30 | 40 | | |
| 47 | 500 | 5 | 10 | | |
| 48 | 8 | 100 | 100 | 100 | 95 |
| 49 | 500 | 100 | 100 | | |
| 50 | 500 | 100 | 100 | | |
| 51 | 100 | 40 | 60 | | |
| 52 | 500 | 100 | 95 | | |
| 53 | 500 | 100 | 10 | | |
| 54 | 500 | 100 | 85 | | |
| 55 | 500 | 100 | 80 | | |
| 56 | 500 | 100 | 100 | | |
| 57 | 250 | 100 | 100 | | |
| 58 | 500 | 100 | 40 | | |
| 59 | 500 | 100 | 100 | | |
| 60 | 200 | 100 | 60 | | |
| 61 | 32 | 45 | 100 | 55 | 90 |
| 62 | 500 | 95 | 95 | | |
| 63 | 500 | 100 | 95 | | |
| 64 | 500 | 100 | 100 | | |
| 65 | 500 | 100 | 100 | | |
| 66 | 500 | 100 | 100 | | |
| 67 | 500 | 85 | 95 | | |
| 68 | 500 | 100 | 0 | | |
| 69 | 8 | 100 | 60 | 5 | 100 |
| 70 | 500 | 100 | 100 | | |
| 71 | 200 | 60 | 10 | | |
| 72 | 200 | 100 | 30 | | |
| 73 | 500 | 100 | 90 | | |
| 74 | 500 | 100 | 80 | | |
| 75 | 200 | 100 | 45 | | |
| 76 | 200 | 95 | 100 | | |
| 77 | 500 | 80 | | | |
| | 200 | 0 | 95 | | |
| 78 | 500 | 90 | 55 | | |
| 79 | 200 | 95 | 60 | | |
| 80 | 500 | 100 | 100 | | |
| 81 | 250 | 100 | 100 | | |
| 82 | 128 | 100 | 90 | | |
| 83 | 250 | 85 | 100 | | |
| 84 | 100 | 100 | 90 | | |
| 85 | 200 | 100 | 100 | | |
| 86 | 16 | 95 | 95 | 40 | 100 |
| 87 | 500 | 100 | 100 | | |
| 88 | 100 | 100 | 25 | 10 | 85 |
| 89 | 200 | 100 | 100 | | |
| 90 | 16 | 100 | 100 | 100 | 90 |
| 91 | 32 | 100 | 100 | 100 | 100 |
| 92 | 500 | 100 | 100 | | |
| 93 | 500 | 100 | 100 | | |
| 94 | 500 | 100 | 100 | | |
| 95 | 200 | 100 | 90 | | |
| 96 | 32 | 100 | 100 | 85 | 95 |
| 97 | 8 | 100 | 100 | 85 | |
| 98 | 16 | 100 | 40 | 35 | 80 |
| 99 | 16 | 100 | 100 | 90 | 85 |
| 100 | 32 | 100 | 100 | 100 | 100 |
| 101 | 1000 | 100 | 100 | | |
| 102 | 128 | 100 | 100 | | |
| 103 | 16 | 90 | 95 | 15 | 100 |
| 105 | 16 | 100 | 100 | | |
| 106 | 256 | 100 | 70 | | |
| 107 | 1000 | 45 | 0 | | |
| 108 | 1000 | 100 | 75 | | |
| 109 | 1000 | 0 | 0 | | |
| 110 | 1000 | 70 | 0 | | |
| 111 | 1000 | 0 | 0 | | |
| 112 | 1000 | 100 | 90 | | |
| 113 | 1000 | 100 | 10 | | |
| 114 | 1000 | 100 | 30 | | |
| 115 | 1000 | 100 | 15 | | |
| 116 | 500 | 100 | 100 | | |
| 117 | 500 | 55 | 0 | | |
| 118 | 500 | 100 | 100 | | |
| 119 | 500 | 100 | 95 | | |
| 120 | 500 | 100 | 100 | | |
| 121 | 500 | 95 | 100 | | |
| 122 | 64 | 100 | 100 | | |
| 123 | 64 | 15 | 0 | | |
| 124 | 64 | 100 | 100 | | |
| 125 | 64 | 100 | 100 | | |
| 240 | 128 | | 65 | | |
| 246 | 128 | | 100 | | |
| 250 | 128 | | 75 | | |
| 276 | 500 | 100 | 100 | | |
| 277 | 128 | 100 | 90 | | |
| 278 | 128 | 100 | 5 | | |
| 279 | 1000 | 100 | 0 | | |
| 280 | 64 | 100 | 100 | | |
| 281 | 32 | 100 | 80 | | |
| 282 | 500 | 100 | 100 | | |
| 283 | 500 | 100 | 100 | | |
| 284 | 64 | 100 | 55 | | |
| 285 | 64 | 100 | 95 | | |
| 286 | 500 | 100 | 100 | | |
| 287 | 750 | 100 | 100 | | |
| 288 | 256 | 100 | 0 | | |
| 289 | 256 | 80 | 0 | | |
| 290 | 256 | 5 | 0 | | |
| 294 | 500 | 100 | 0 | | |
| 295 | 500 | 0 | 65 | | |
| 297 | 500 | 100 | 100 | | |
| 300 | 500 | 100 | 15 | | |
| 301 | 500 | 100 | 75 | | |
| 302 | 500 | 100 | 40 | | |
| 303 | 128 | 100 | 85 | | |
| 304 | 500 | 90 | 85 | | |
| 305 | 128 | 85 | 35 | | |
| 306 | 250 | 100 | 85 | | |
| 307 | 500 | 100 | 90 | | |
| 308 | 500 | 100 | 60 | | |
| 309 | 500 | 100 | 80 | | |
| 310 | 500 | 100 | 100 | | |
| 311 | 200 | 0 | 75 | | |
| 312 | 8 | 95 | 100 | 100 | 100 |
| 313 | 16 | 100 | 95 | 85 | 100 |
| 314 | 64 | 100 | 100 | | |
| 315 | 8 | 100 | 100 | 100 | 100 |
| 316 | 4 | 100 | 100 | 100 | 100 |
| 317 | 64 | | 25 | | |
| 318 | 64 | 100 | 100 | | |
| 319 | 8 | 95 | 85 | 95 | 95 |
| 320 | 16 | 100 | 75 | 35 | 15 |
| 321 | 64 | 5 | 20 | | |
| 322 | 64 | 75 | 40 | | |
| 323 | 8 | 100 | 100 | 100 | 100 |
| 324 | 8 | 100 | 100 | 100 | 100 |
| 325 | 1000 | 20 | 40 | | |
| 326 | 64 | 30 | 100 | | |
| 328 | 500 | 100 | 100 | | |
| 329 | 500 | 100 | 100 | | |
| 330 | 8 | 100 | 100 | 80 | 95 |
| 331 | 500 | 100 | 100 | | |
| 332 | 16 | 100 | 95 | 85 | 95 |
| 333 | 500 | 100 | 100 | | |
| 334 | 500 | 100 | 100 | | |
| 335 | 128 | | 55 | | |
| 336 | 128 | | 70 | | |

MBB = Mexican bean beetle
SAW = southern armyworm
BAW = beet armyworm
CL = cabbage looper

What is claimed is:
1. An insecticidal pyrazoline of the formula

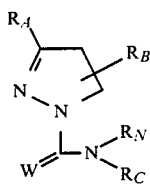

wherein
$R_A$ is of the formula

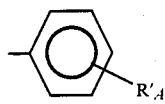
(I)

in which $R'_A$ is selected from hydrogen, halogen, lower alkyl, lower alkoxy, lower haloalkoxy, lower alkynyloxy and lower haloalkyl; or $R_A$ is of the formula

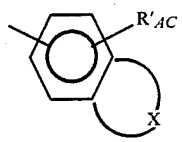
(II)

in which X is a bridge of the formula

wherein a is 1-3, a' is 0 or 1, a+a' is at least 2 but no greater than 3, $R'_{AA}$ and $R'_{AB}$ are independently selected from hydrogen, halogen and lower alkyl, and $R'_{AC}$ is selected from hydrogen, halogen, lower alkyl, lower alkoxy, lower haloalkoxy, and lower haloalkyl;
$R_B$ is a 4- or 5-substituent of the formula

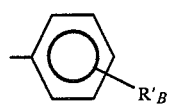
(III)

in which $R'_B$ is selected from hydrogen, halogen, lower alkyl, lower alkoxy, and lower haloalkyl; or $R_B$ is of the formula

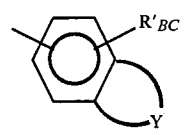
(IV)

in which Y is a bridge of the formula

wherein b is 1-3, b' is 0 or 1, b+b' is at least 2 but no greater than 3, $R'_{BA}$ and $R'_{BB}$ are independently selected from hydrogen, halogen and lower alkyl, and $R'_{BC}$ is selected from hydrogen, halogen, lower alkyl, lower alkoxy, lower haloalkoxy, and lower haloalkyl;
$R_C$ is of the formula

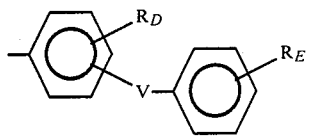
(V)

or

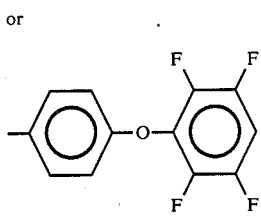

in which $R_D$ is selected from hydrogen and lower alkyl; $R_E$ is selected from halogen, alkoxy, containing 1-4 carbon atoms, lower haloalkoxy, lower haloalkyl, cyano, nitro, phenyl, phenoxy, benzoyl, benzoyloxy, —$NR_FR_G$ wherein $R_F$ and $R_G$ are independently lower alkyl, and —$SO_nR_H$ wherein $R_H$ is lower alkyl and n is 0-2; or $R_C$ is of the formula

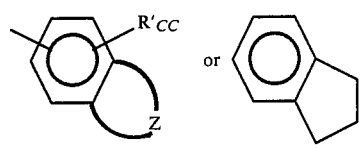
(VI)

in which Z is a bridge of the formula

wherein c is 1-3, c' is 0 or 1, c+c' is at least 2 but no greater than 3, $R'_{CA}$ and $R'_{CB}$ are independently selected from hydrogen, halogen and lower alkyl, with the proviso that $R'_{CA}$ and $R'_{CB}$ are not both hydrogen when c is 1 and c' is 1, and $R'_{CC}$ is selected from hydrogen, halogen, lower alkyl, lower alkoxy, lower haloalkoxy, and lower haloalkyl; provided that when $R_A$ is a compound of group I and $R_B$ is a compound of group III, $R_C$ is not a compound of group V;
$R_N$ is hydrogen or lower alkyl; and
V and W are independently oxygen or sulfur.

2. A compound of claim 1 wherein W is oxygen.

3. A compound of claim 1 wherein $R'_A$ is halogen or lower haloalkoxy.

4. A compound of claim 1 wherein $R_B$ is a 4-substituent.

5. A compound of claim 1 wherein $R_B$ is of the formula

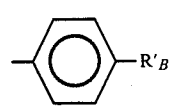

6. A compound of claim 5 wherein $R'_B$ is halogen.

7. A compound of claim 1 wherein $R_C$ is of the formula

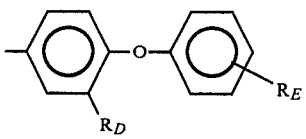

or is selected from 2,3-dihydro-2,2-dimethylbenzofuran-5-yl, 2,3-dihydro-2,2,3,3-tetrafluorobenzofuran-5-yl, 2,3-dihydro-2,2,3,3-tetrafluorobenzofuran-6-yl, 2,2-difluoro-1,3-benzodioxol-5-yl, and 2,2-dimethyl-1,3-benzodioxol-5-yl.

8. A compound of claim 1 wherein $R_C$ is of the formula

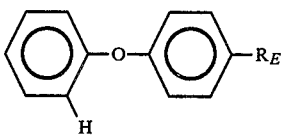

9. A compound of claim 8 wherein $R_E$ is lower haloalkoxy.

10. 3-(4-Difluoromethoxyphenyl)-N-(2,3-dihydro-2,2-dimethylbenzofuran-5-yl)-4-phenylpyrazoline-1-carboxamide, a compound of claim 1.

11. 3,4-bis(4-Fluorophenyl)-N-(2,3-dihydro-2,2,3,3-tetrafluorobenzofuran-5-yl)pyrazoline-1-carboxamide, a compound of claim 1.

12. 3,4-bis(4-Fluorophenyl)-N-(2,3-dihydro-2,2-dimethylbenzofuran-5-yl)pyrazoline-1-carboxamide, a compound of claim 1.

13. N-(2,3-Dihydro-2,2,3,3-tetrafluorobenzofuran-5-yl)-3-(4-difluoromethoxyphenyl -4-phenylpyrazoline-1-carboxamide, a compound of claim 1.

14. N-(2,2-Difluoro-1,3-benzodioxol-5-yl)-3-(4-difluoromethoxyphenyl)-N-methyl-4-phenylpyrazoline-1-carboxamide, a compound of claim 1.

15. 3,4-bis(4-Chlorophenyl)-N-(2,2-dimethyl-1,3-benzodioxol-5-yl)pyrazoline-1-carboxamide, a compound of claim 1.

16. N-(2,2-Difluoro-1,3-benzodioxol-5-yl)-3,4-bis-(4-fluorophenyl)pyrazoline-1-carboxamide, a compound of claim 1.

17. 3-(4-Chlorophenyl)-N-(2,2-difluoro-1,3-benzodioxol-5-yl)-4-(4-fluorophenyl)pyrazoline-1-carboxamide, a compound of claim 1.

18. 3-(4-Difluoromethoxyphenyl)-N-(2,3-dihydro-2,2,3,3-tetrafluorobenzofuran-5-yl)-N-methyl-4-phenylpyrazoline-1-carboxamide, a compound of claim 1.

19. 3-(4-Difluoromethoxyphenyl)-4-(4-fluorophenyl)-N-(2,3-dihydro-2,2,3,3,-tetrafluorobenzofuran-5-yl)pyrazoline-1-carboxamide, a compound of claim 1.

20. 3-(4-Difluoromethoxyphenyl)-4-(4-fluorophenyl)-N-(2,3-dihydro-2,2,3,3-tetrafluorobenzofuran-6-yl)pyrazoline-1-carboxamide, a compound of claim 1.

21. 4-(4-Chlorophenyl)-N-(2,3-dihydro-2,2-dimethylbenzofuran-5-yl)-3-phenylpyrazoline-1-carboxamide, a compound of claim 1.

22. 3-(4-Chlorophenyl)-4-(4-fluorophenyl)-N-(2,3-dihydro-2,2-dimethylbenzofuran-5-yl)pyrazoline-1-carboxamide, a compound of claim 1.

23. 3-(4-Difluoromethoxyphenyl)-4-(4-fluorophenyl)-N-(2,3-dihydro-2,2-dimethylbenzofuran-5-yl)pyrazoline-1-carboxamide, a compound of claim 1.

24. 4-(4-Chlorophenyl)-3-(4-difluoromethoxyphenyl)-N-(2,3-dihydro-2,2-dimethylbenzofuran-5-yl)pyrazoline-1-carboxamide, a compound of claim 1.

25. 3,4-bis(4-Chlorophenyl)-N-(2,2-difluoro-1,3-benzodioxol-5-yl)pyrazoline-1-carboxamide, a compound of claim 1.

26. 3,4-bis(4-Chlorophenyl)-N-(2,3-dihydro-2,2-dimethylbenzofuran-5-yl)pyrazoline-1-carboxamide, a compound of claim 1.

27. 3-(4-Chlorophenyl)-N-(2,3-dihydro-2,2-dimethylbenzofuran-5-yl)-4-phenylpyrazoline-1-carboxamide, a compound of claim 1.

28. 3-(4-Chlorophenyl)-4-phenyl-N-[4-(4-trifluoromethylphenoxy)phenyl]pyrazonline-1-carboxamide.

29. An insecticidal composition comprising an insecticidally effective amount of a compound of claim 1 in admixture with a compatible, agriculturally acceptable carrier, diluent, adjuvant, or complementary pesticide.

30. A composition of claim 29 wherein W is oxygen.

31. A composition of claim 29 wherein $R'_A$ is halogen or lower haloalkoxy.

32. A composition of claim 29 wherein $R_B$ is a 4-substituent.

33. A method for controlling insects which comprises applying to the locus where control is desired an insecticidally effective amount of a compound of claim 1.

* * * * *